US012324769B1

(12) United States Patent
Zhang et al.

(10) Patent No.: US 12,324,769 B1
(45) Date of Patent: Jun. 10, 2025

(54) DOUBLE-NETWORK VERSATILE HYDROGEL WITH ANTIBACTERIAL AND DRUG SEQUENTIAL RELEASE CAPABILITIES

(71) Applicant: Eye Institute of Shandong First Medical University, Shandong (CN)

(72) Inventors: Hengrui Zhang, Shandong (CN); Qingjun Zhou, Shandong (CN); Shuqin Meng, Shandong (CN); Huifang Ren, Shandong (CN)

(73) Assignee: EYE INSTITUTE OF SHANDONG FIRST MEDICAL UNIVERSITY (CN)

( * ) Notice: Subject to any disclaimer, the term of this patent is extended or adjusted under 35 U.S.C. 154(b) by 0 days.

(21) Appl. No.: 18/913,776

(22) Filed: Oct. 11, 2024

(30) Foreign Application Priority Data

Nov. 29, 2023 (CN) .......................... 202311609694.4

(51) Int. Cl.
| | |
|---|---|
| *A61F 9/00* | (2006.01) |
| *A61L 27/12* | (2006.01) |
| *A61L 27/18* | (2006.01) |
| *A61L 27/20* | (2006.01) |
| *A61L 27/22* | (2006.01) |

(Continued)

(52) U.S. Cl.
CPC ............ *A61F 9/0017* (2013.01); *A61L 27/12* (2013.01); *A61L 27/18* (2013.01); *A61L 27/20* (2013.01); *A61L 27/227* (2013.01); *A61L 27/3687* (2013.01); *A61L 27/52* (2013.01)

(58) Field of Classification Search
CPC .................................................... A61F 9/0017
See application file for complete search history.

(56) References Cited

U.S. PATENT DOCUMENTS

2012/0071580 A1* 3/2012 Cho ........................ A61L 27/14
523/105

FOREIGN PATENT DOCUMENTS

| CN | 113648455 A | 11/2021 |
|---|---|---|
| CN | 113698560 A | 11/2021 |
| CN | 114225096 A | 3/2022 |
| CN | 114796604 A | 7/2022 |
| CN | 115105629 A | 9/2022 |

(Continued)

OTHER PUBLICATIONS

Meng, et al. "A Versatile Hydrogel with Antibacterial and Sequential Drug-Releasing Capability for the Programmable Healing of Infectious Keratitis" ACS Nano, vol. 17, Issue 23. Date of issue: Dec. 3, 2023.

(Continued)

*Primary Examiner* — Carlos A Azpuru
(74) *Attorney, Agent, or Firm* — FOLEY & LARDNER LLP

(57) ABSTRACT

A preparation method of a double-network versatile hydrogel with antibacterial and drug sequential release capabilities is provided in the present disclosure, belonging to the technical field of biological corneas. The preparation method includes the following steps: mixing filipin protein-methacrylate, glycidyl methacrylate functionalized quaternized chitosan, polydeoxyribonucleotide, and lithium phenyl(2,4,6-trimethylbenzoyl) phosphinate with drug-loaded micelles, followed by cross-linking under irradiation of ultraviolet to construct a double-network versatile hydrogel with antibacterial and drug sequential release capabilities.

7 Claims, 45 Drawing Sheets

(51) Int. Cl.
*A61L 27/36* (2006.01)
*A61L 27/52* (2006.01)

(56) References Cited

FOREIGN PATENT DOCUMENTS

| CN | 115154672 A | 10/2022 |
|---|---|---|
| IN | 201617016473 A | 8/2016 |
| KR | 20200020423 A | 11/2020 |
| SG | 133903 A1 | 8/2007 |

OTHER PUBLICATIONS

Meng-Shuang, et al. "Studies on a new nanomicelle curcumin ophthalmic solution: preparation and characterizations in vitro /in vivo" New progress in ophthalmology, issue 10. Date of issue: Oct. 25, 2016.

Yangyingfan, et al. "Evaluation of Bio-functionalized Polyethylene Glycol (PEG)-Based Composite Hydrogels in Infected Wound Healing" Journal of Huazhong University of Science and Technology (Medical Edition), No. 04. Date of issue: Aug. 15, 2020.

Search Report and English translation for Chinese Patent Application No. 202311609694.4, mailed Mar. 27, 2024, 8 pg.

Search Report and English translation for Chinese Patent Application No. 202311609694.4, mailed Apr. 10, 2024, 4 pg.

Notification of Grant Patent Right for Invention and English translation for Chinese Patent Application No. 202311609694.4, mailed Apr. 17, 2024, 3 pg.

Notice of First Office Action and English translation for Chinese Patent Application No. 232311609694.4, mailed Apr. 1, 2024, 7 pg.

* cited by examiner

DOUBLE-NETWORK VERSATILE HYDROGEL WITH ANTIBACTERIAL AND DRUG SEQUENTIAL RELEASE CAPABILITIES

CROSS-REFERENCE TO RELATED APPLICATIONS

This application claims priority to Chinese Patent Application No. 202311609694.4, filed on Nov. 29, 2023, the contents of which are hereby incorporated by reference.

TECHNICAL FIELD

The present disclosure belongs to the technical field of biological corneas, and particularly relates to a preparation method of a double-network versatile hydrogel with antibacterial and drug sequential release capabilities.

BACKGROUND

Infectious keratitis is an inflammatory corneal lesion caused by pathogenic microorganisms invading the cornea. About 20% of the blindness in the world are caused by corneal infection, which has become one of the common blinding eye diseases in the world. Antibiotic medication is the first-line therapy for the clinical management of infectious keratitis; however, in the presence of drug-resistant bacterial infections, medication does not achieve the desired therapeutic effect. In case of ineffective medication, selective replacement of diseased corneal tissue is considered to be the most effective method of controlling the infection and restoring transparency to the corneal tissue, but there are conditions such as donor corneas, advanced surgical skills, and specialized equipment required for corneal transplantation. In addition, complete excision of the infected tissue requires a large donor cornea to be transplanted, which carries a high risk of rejection and failure, and thus there is an urgent need to develop donor corneal substitutes.

Hydrogel is a three-dimensional (3D) network with water retention capacity, good hydrophilicity, transparency and biocompatibility, and is also a three-dimensional porous structure that promotes cellular activity and metabolite transport, suitable for regeneration and repair of damaged corneal tissue. Zhao et al. designed a double network hydrogel based on GelMA and oxidized dextran (ODEX), which has excellent mechanical strength and adhesion to form a tight bond between the hydrogel and the recipient corneal bed. Li et al. combined Pluronic F127diacrylate (F127DA) nano-micelle loaded with type I collagen (COL I) with GelMA to improve the modulus of hydrogel and endow hydrogel with excellent tissue adhesion. However, the physiological environment of infectious keratitis is more complicated, which requires hydrogel cornea to have multiple functions of antibacterial, anti-inflammatory, proliferation-promoting and scar-resisting. Nonetheless, most of the hydrogel corneas reported so far focus on regulating corneal regenerative function, which is not capable of meeting the demand for corneal transplantation for infectious keratitis.

SUMMARY

In order to address the problem that current hydrogel-based corneal substitutes are mainly designed to promote a single stage of corneal regeneration, which is insufficient to meet the needs of clinical management of severe infectious keratitis, including multiple stages of corneal wound healing, the present disclosure provides a preparation method of a double-network versatile hydrogel (SQPV) with antibacterial and drug sequential release capabilities. The versatile hybrid hydrogel is prepared by using silk fibroin (SF) and chitosan (CS) as the main raw materials, which has spatiotemporal properties of drug release, and is capable of realizing antimicrobial, anti-inflammatory, proliferative, and remodeling functions at different stages of corneal infection repair, respectively, and realizing controllable spatiotemporal sequential administration of the drug. In addition, the SQPV has mechanical strength and transparency similar to that of a natural cornea. In vitro and in vivo studies have also confirmed that the SQPV provided by the present disclosure is effective in eliminating residual bacteria, reducing inflammation, promoting regeneration of the corneal epithelium and stroma, preventing corneal scar formation, and ultimately accelerating wound healing.

In order to achieve the above objectives, the present disclosure provides the following technical schemes.

One of the technical schemes of the present disclosure is to provide a preparation method of a double-network versatile hydrogel with antibacterial and drug sequential release capabilities, including the following steps:

mixing methacrylate silk fibroin (SFMA), glycidyl methacrylate functionalized quaternized chitosan (QCSG), polydeoxyribonucleotide (PDRN), and lithium phenyl (2,4,6-trimethylbenzoyl) phosphinate (LAP) with drug-loaded micelles, followed by cross-linking under irradiation of ultraviolet to construct a double-network versatile hydrogel with antibacterial and drug sequential release capabilities;

preparation steps of the drug-loaded micelles include:

step 1, firstly mixing 4-(4-hydroxymethyl-2-methoxy-5-nitrophenoxy) butanoic acid (NBA), tert-butoxycarbonyl-polyethylene glycol-amino (BOC-NH-PEG-NH$_2$) and 1H-benzotriazol-1-yloxytripyrrolidino-phosphonium hexafluorophosphate (PyBOP) in a solvent, and adding trifluoroacetic acid (TFA) for reaction, and then concentrating and precipitating in a pre-cooled diethyl ether to obtain a precipitate (NB-PEG-NH$_2$);

step 2, re-dissolving the precipitate obtained in step 1, mixing with D/L-lactide, glycoluril and stannous octoate [Sn(Oct)$_2$], concentrating after a reaction, and precipitating in a pre-cooled diethyl ether to obtain a precipitate (PLGA-PEG-NB); and step 3, co-blending the precipitate obtained from step 2 with the drug in a solvent and stirring to obtain the drug-loaded micelles.

The SFMA and QCSG in the present disclosure are both prepared according to the methods disclosed in the prior art, specifically as follows:

preparation of SFMA (see FIG. 1 for the synthesis roadmap)

extracting SF from silkworm cocoons, boiling in 0.02 Mile (M) sodium carbonate for 30 minutes (min) to remove sericin; dissolving the sericin-removed SF in 9.3 M lithium bromide solution for 1 hour (h); introducing glycidyl methacrylate (GMA) into the mixture and stirring at 60 degrees Celsius (° C.) for 8 h, dialyzing the reaction mixture in distilled water for 5 days to obtain the desired SFMA;

preparation of QCSG (see FIG. 2 for the synthesis roadmap)

dissolving 0.5 gram (g) of chitosan in 20 milliliters (mL) of deionized water, dropwise adding 2 equivalents of glycidyltrimethylammonium chloride (GTMAC), and stirring at 55° C. for 18 h; adding GMA to the reaction mixture, and stirring at 55° C. for 15 h; and, finally, precipitating by pre-cooled acetone, dialyzing in distilled water, and lyophilizing to obtain QCSG.

Optionally, a mass ratio of the SF-methacrylate to the glycidyl methacrylate functionalized quaternized chitosan is 5:1; an addition amount of polydeoxyribonucleotide is 0.01% of the total mass of the SF-methacrylate and glycidyl methacrylate functionalized quaternized chitosan; an addition amount of the lithium phenyl(2,4,6-trimethylbenzoyl) phosphinate is 0.2% of the total mass of the SF-methacrylate and glycidyl methacrylate functionalized quaternized chitosan; an addition amount of the drug-loaded micelles does not exceed 1% of the total mass of the SF-methacrylate and glycidyl methacrylate functionalized quaternized chitosan.

Optionally, a wavelength of the ultraviolet is 405 nanometers (nm) and a power is 3 Watts (W).

Optionally, in the preparation steps of the drug-loaded micelles, a mass ratio of raw materials is: 4-(4-hydroxymethyl-2-methoxy-5-nitrophenoxy) butyric acid:tert-butoxycarbonyl-polyethylene glycol-amino:1H-benzotriazol-1-yloxytripyrrolidinophosphonium hexafluorophosphate: trifluoroacetic acid:D/L-lactide:glycoluril:stannous isooctoate=0.25:5:1.5:0.15:0.2:0.05:0.005.

Optionally, in the preparation step of the drug-loaded micelles, a mass ratio of the precipitate obtained in the step 2 to the drug is 5:1.

Optionally, in the preparation steps of the drug-loaded micelles, a reaction duration in the step 1 is 1 h; a reaction temperature in the step 2 is 130° C. and a reaction duration is 12 h.

Another technical scheme of the present disclosure is to provide a double-network versatile hydrogel with antibacterial and drug sequential release capabilities, prepared according to the preparation method of the double-network versatile hydrogel with antibacterial and drug sequential release capabilities.

Another technical scheme of the present disclosure is to provide an application of the double-network versatile hydrogel with antibacterial and drug sequential release capabilities in biological corneas.

The beneficial technical effects of the present disclosure are as follows.

The present disclosure provides a preparation method of a double-network versatile hydrogel with antibacterial and drug sequential release capabilities, which significantly improves the physical and chemical properties of the hydrogel and makes it an ideal substitute material for corneal transplantation. The double-network versatile hydrogel prepared by the present disclosure shows transparency and mechanical strength similar to that of natural cornea, as well as extremely strong adhesion strength, and is capable of realizing antibacterial, anti-inflammatory, proliferative, and remodeling functions at different stages of corneal infection repair, respectively, and realizing controlled spatio-temporal sequential administration of drugs. The double-network versatile hydrogel provided by the present disclosure has great application potential in corneal repair and regeneration of severe bacterial keratitis.

DETAILED DESCRIPTION OF THE EMBODIMENTS

A number of exemplary embodiments of the present disclosure are now e described in detail, and this detailed description should not be considered as a limitation of the present disclosure, but should be understood as a rather detailed description of certain aspects, characteristics and embodiments of the present disclosure. It should be understood that the terminology described in the present disclosure is only for describing specific embodiments and is not used to limit the present disclosure.

In addition, for the numerical range in the present disclosure, it should be understood that each intermediate value between the upper limit and the lower limit of the range is also specifically disclosed. Intermediate values within any stated value or stated range, as well as each smaller range between any other stated value or intermediate values within the stated range are also included in the present disclosure. The upper and lower limits of these smaller ranges can be independently included or excluded from the range.

Unless otherwise specified, all technical and scientific terms used herein have the same meaning as commonly understood by one of ordinary skill in the art to which this present disclosure relates. Although the present disclosure only describes the preferred methods and materials, any methods and materials similar or equivalent to those described herein can also be used in the practice or testing of the present disclosure.

The terms "including", "comprising", "having" and "containing" used in this specification are all open terms, which means including but not limited to.

Embodiment 1

Preparation of SQPV Hydrogel (1) Preparation of SFMA:

SF is extracted from silkworm cocoons, boiled in 0.02 M sodium carbonate for 30 min, and sericin is removed; sericin-removed SF is dissolved in 9.3 M lithium bromide solution for 1 h; then GMA is introduced into the mixture and stirred at 60° C. for 8 h; the reaction mixture is dialyzed in distilled water for 5 days to obtain the desired SFMA.

(2) Preparation of QCSG: 0.5 g chitosan is dissolved in 20 mL deionized water, 2 equivalents of GTMAC are added dropwise, and the mixture is stirred at 55° C. for 18 h; then GMA is added to the reaction mixture and stirred at 55° C. for 15 h; finally, QCSG is obtained by precipitation with precooled acetone, dialyzing with distilled water and freeze-drying.

Figure 15:
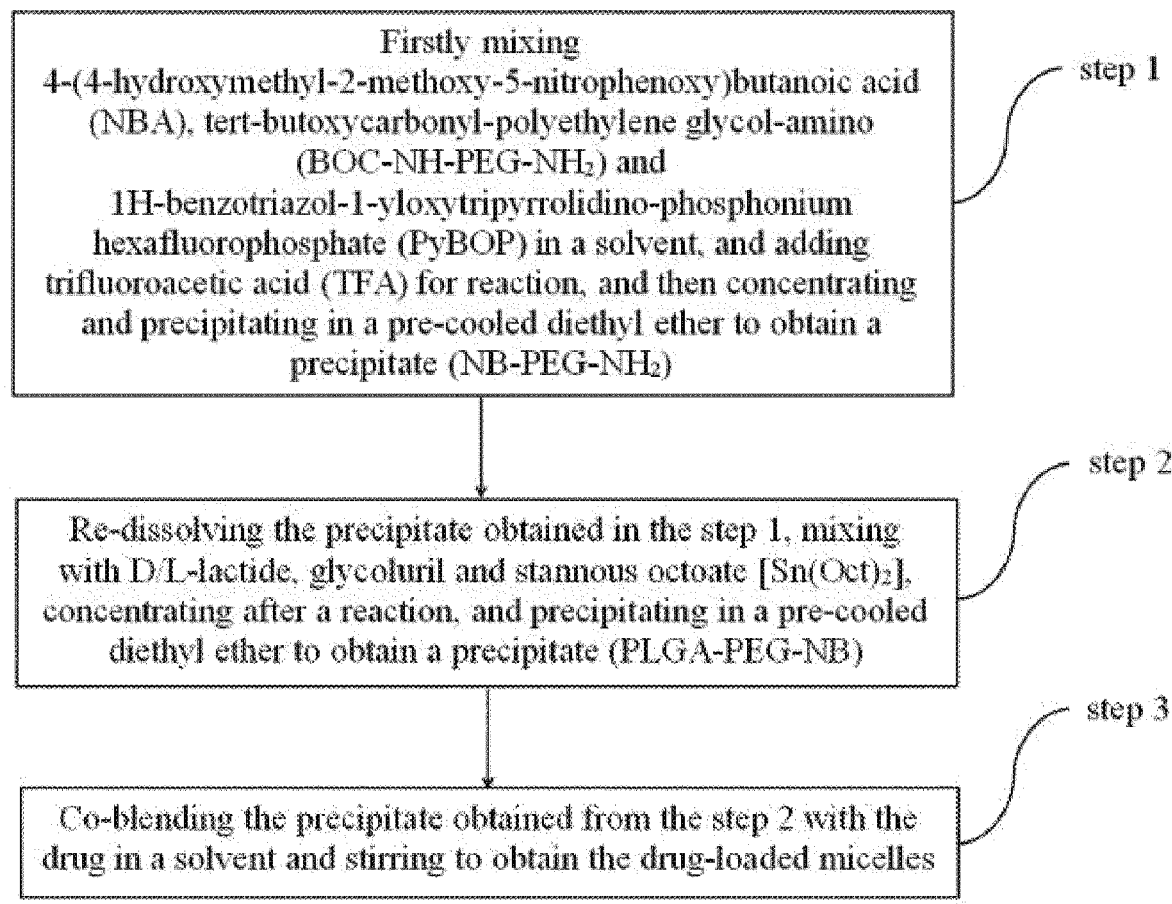
FIG. 15 shows is a process illustrating the preparation steps of the drug-loaded micelles.

(3) Preparation of drug-loaded micelles:

As shown in FIG. 15, the preparation steps of the drug-loaded micelles include:

step 1, firstly mixing 4-(4-hydroxymethyl-2-methoxy-5-nitrophenoxy) butanoic acid (NBA), tert-butoxycarbonyl-polyethylene glycol-amino (BOC-NH-PEG-NH$_2$) and 1H-benzotriazol-1-yloxytripyrrolidino-phosphonium hexafluorophosphate (PyBOP) in a solvent, and adding trifluoroacetic acid (TFA) for reaction, and then concentrating and precipitating in a pre-cooled diethyl ether to obtain a precipitate (NB-PEG-NH$_2$);

step 2, re-dissolving the precipitate obtained in the step 1, mixing with D/L-lactide, glycoluril and stannous octoate [Sn(Oct)$_2$], concentrating after a reaction, and precipitating in a pre-cooled diethyl ether to obtain a precipitate (PLGA-PEG-NB); and step 3, co-blending the precipitate obtained from the step 2 with the drug in a solvent and stirring to obtain the drug-loaded micelles.

Specifically, the preparation of drug-loaded micelles includes:

1. NBA of 0.25 g is added into chloroform solution containing BOC-NH-PEG-NH$_2$ (5 g) and PyBOP (1.5 g), and stirred at room temperature for 30 min, then TFA (0.15 g) is added dropwise into the reaction mixture, and after stirring at room temperature for 1 h, the mixture evaporates and precipitates into precooled ether to obtain NB-PEG-NH$_2$;

2. NB-PEG-NH$_2$ is dissolved in anhydrous toluene at room temperature, and 0.2 g D/L-lactide, 0.05 g glycoluril and 0.005 g Sn(Oct)$_2$ are added to the above solution and stirred at 130° C. for 12 h, and then concentrated in vacuum and precipitated in precooled ether to obtain the product PLGA-PEG-NB;

3. preparation of verteporfin-loaded micelles: 10 mg of PLGA-PEG-NB and 2 mg of verteporfin are dissolved in 1 mL of DMF and stirred away from light for 1 h. Then water (4 mL) is added and stirred vigorously for 30 min, and the resulting solution is dialyzed with deionized water and filtered through a microporous membrane to obtain the drug-loaded micelles; and (4) synthesis of SQPV hydrogel: SFMA and QCSG are completely dissolved in deionized water in a mass ratio of 5:1 to prepare a 9% mixed solution, and PDRN at 0.01% of the total mass of SFMA and QCSG is added, followed by the addition of drug-loaded micelles at 5% of the total mass of SFMA and QCSG and LAP at 0.2% of the total mass of SFMA and QCSG, and then irradiated under ultraviolet (405 nm, 3 W), the converted o-Nitrophenyl Methyl Group in PLGA-PEG-NB micelles reacts with amino groups in QCSG and SFMA to obtain the SQPV hydrogel.

Figure 1:
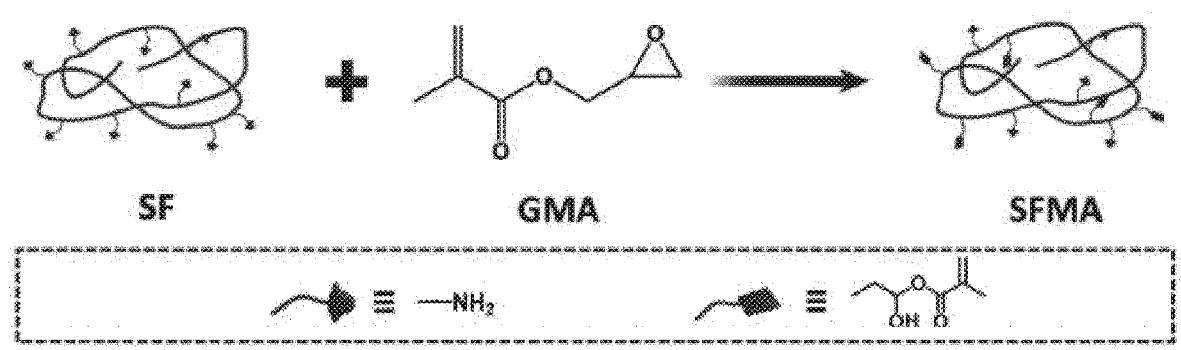
FIG. 1 shows the synthesis roadmap of SFMA.
Figure 2:
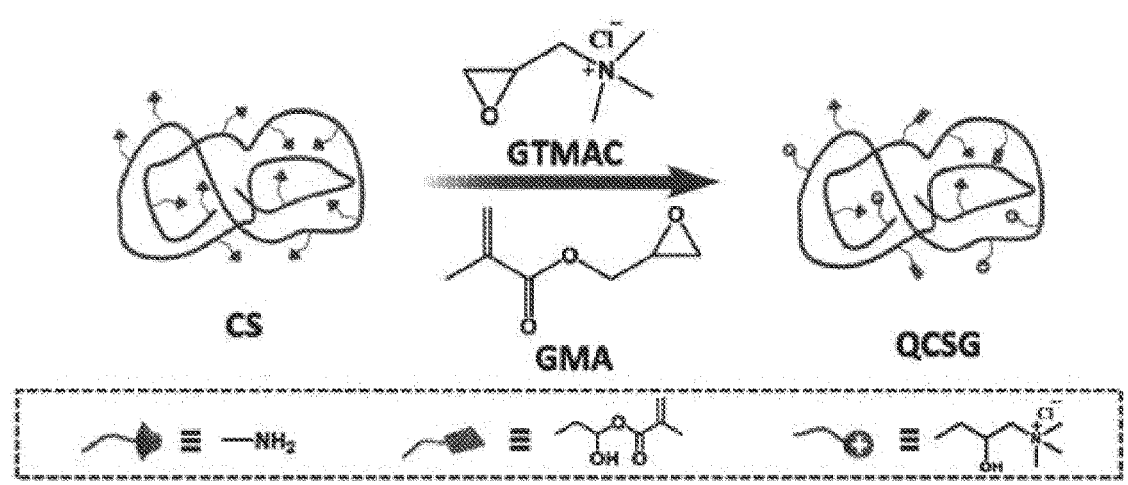
FIG. 2 shows the synthesis roadmap of QCSG.
Figure 3:
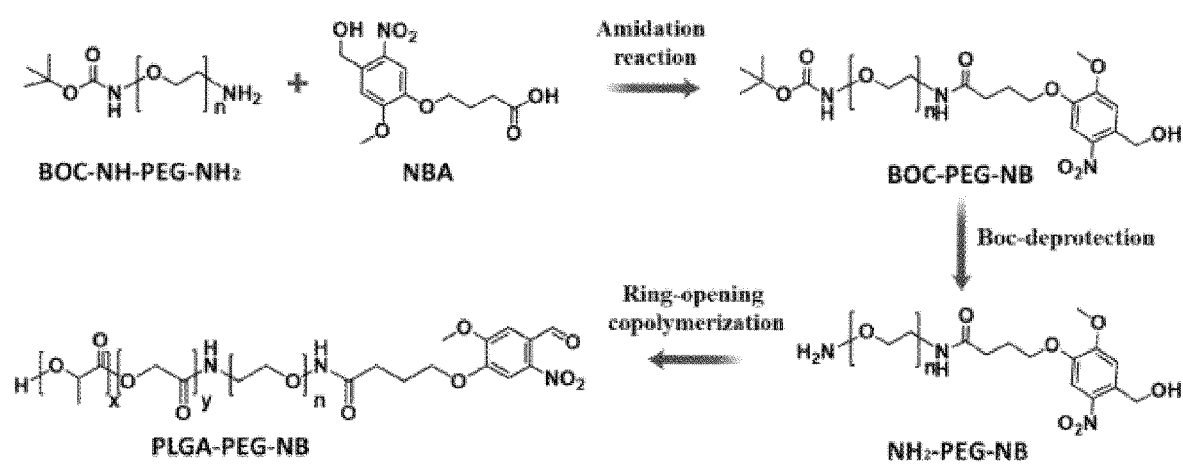
FIG. 3 is the synthesis roadmap of PLGA-PEG-NB.
Figure 4A:
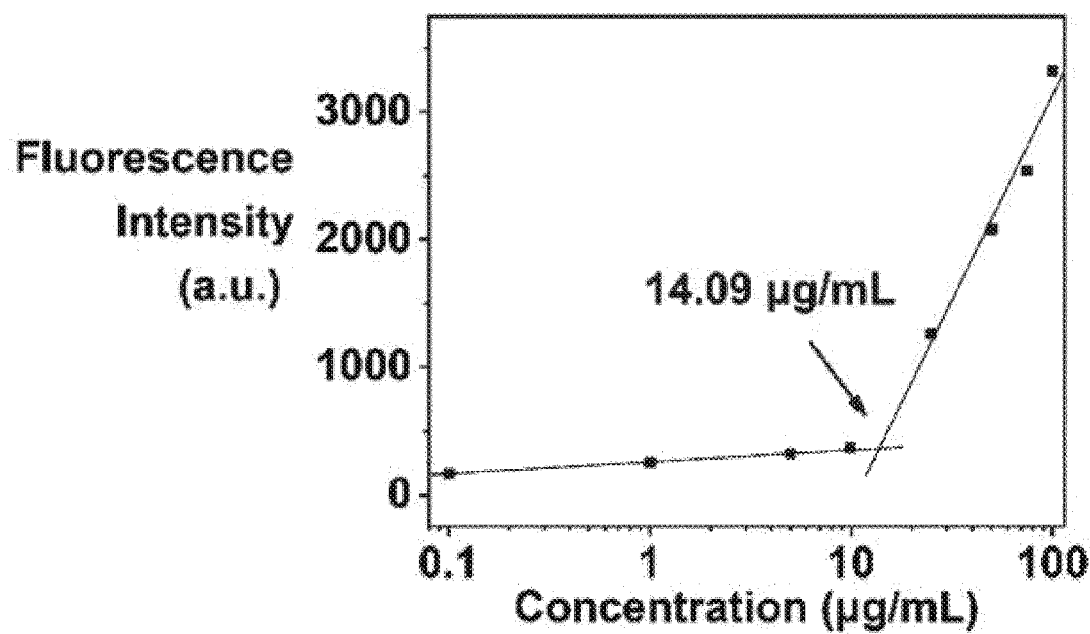
FIG. 4A shows the measurement results of critical micelle concentrations of PLGA-PEG-NB micelles.
Figure 4B:
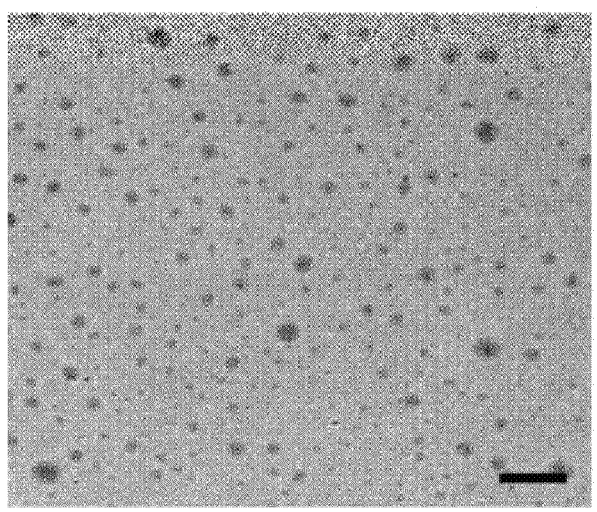
FIG. 4B is the transmission electron microscope (TEM) diagram of drug-loaded micelles.

In order to prove the feasibility of applying double-network hydrogel to corneal wound defect, the SQPV hydrogel prepared in Embodiment 1 (including SQPV hydrogel prepared by adjusting preparation conditions) and the intermediate products thereof are characterized in a series, and the specific results are shown in FIG. 4A-FIG. 4H. Among the figures, FIG. 4A shows the results of the critical micelle concentration measurement of PLGA-PEG-NB micelles as determined by the Nile Red fluorescent probe, which is 14.09 micrograms per milliliter (μg/mL), demonstrating the micelle-forming ability of the amphiphilic copolymer; FIG.

Figure 4C:
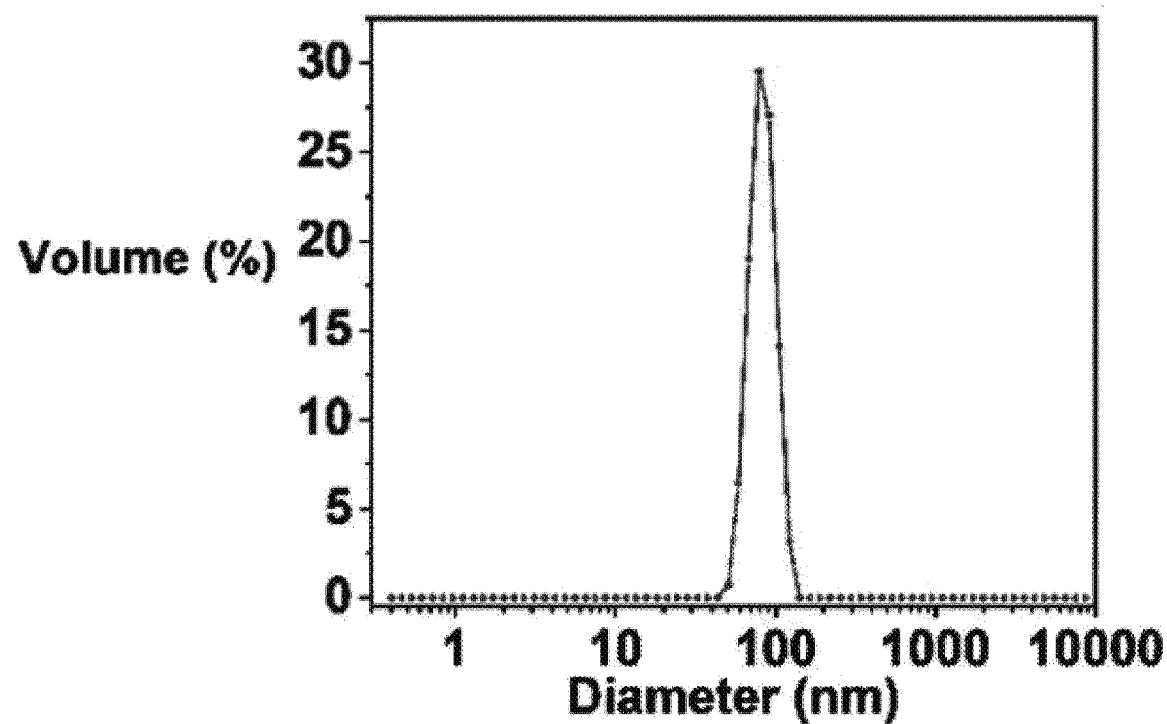
FIG. 4C shows the size distribution diagram of drug-loaded micelles.
Figure 4D:
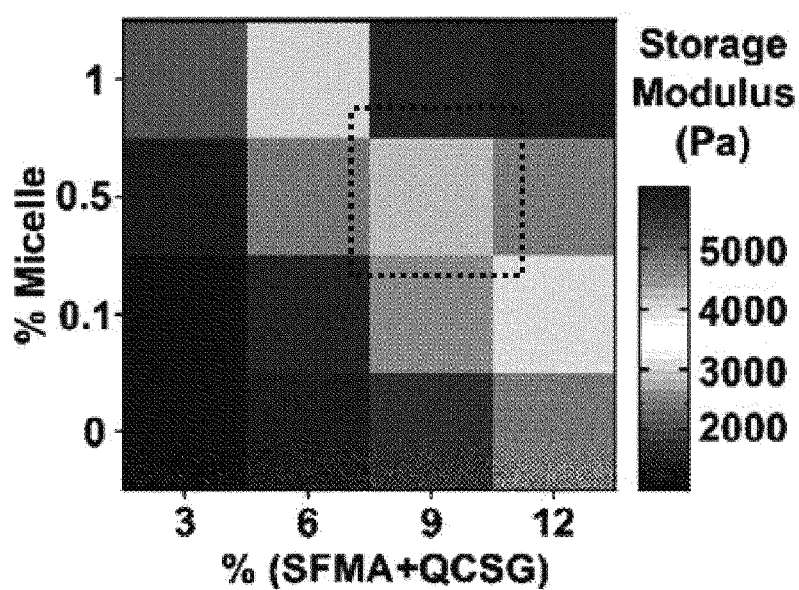
FIG. 4D illustrates the mechanical properties of SQPV hydrogel with different polymer and micelle concentrations.
Figure 4E:
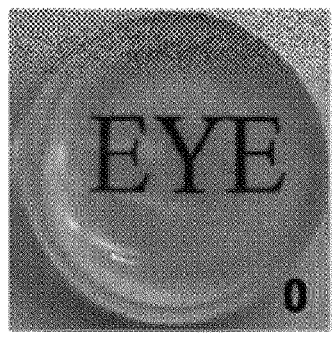
FIG. 4E is the general transparency observation of SQPV hydrogel at different micelle concentrations.
Figure 4E:
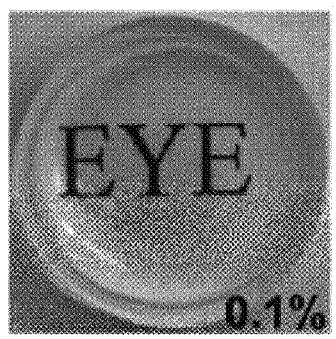
Figure 4E:
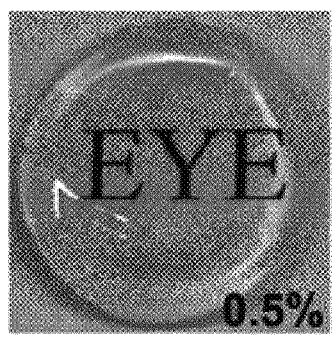
Figure 4E:
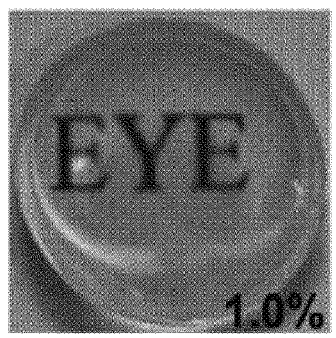
Figure 4F:
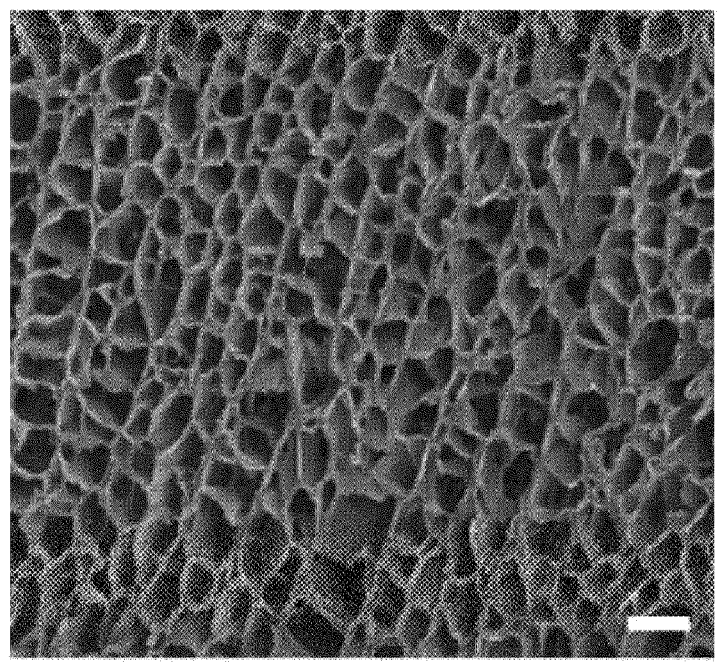
FIG. 4F is the scanning electron microscope (SEM) image of SQPV hydrogel.
Figure 4G:
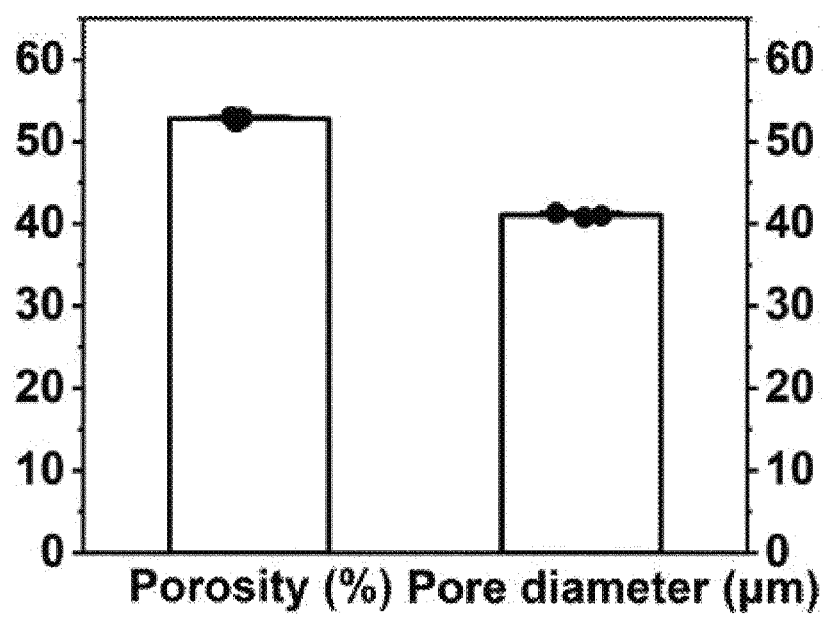
FIG. 4G is the porosity and pore size histogram of SQPV hydrogel based on SEM data.
Figure 4H:
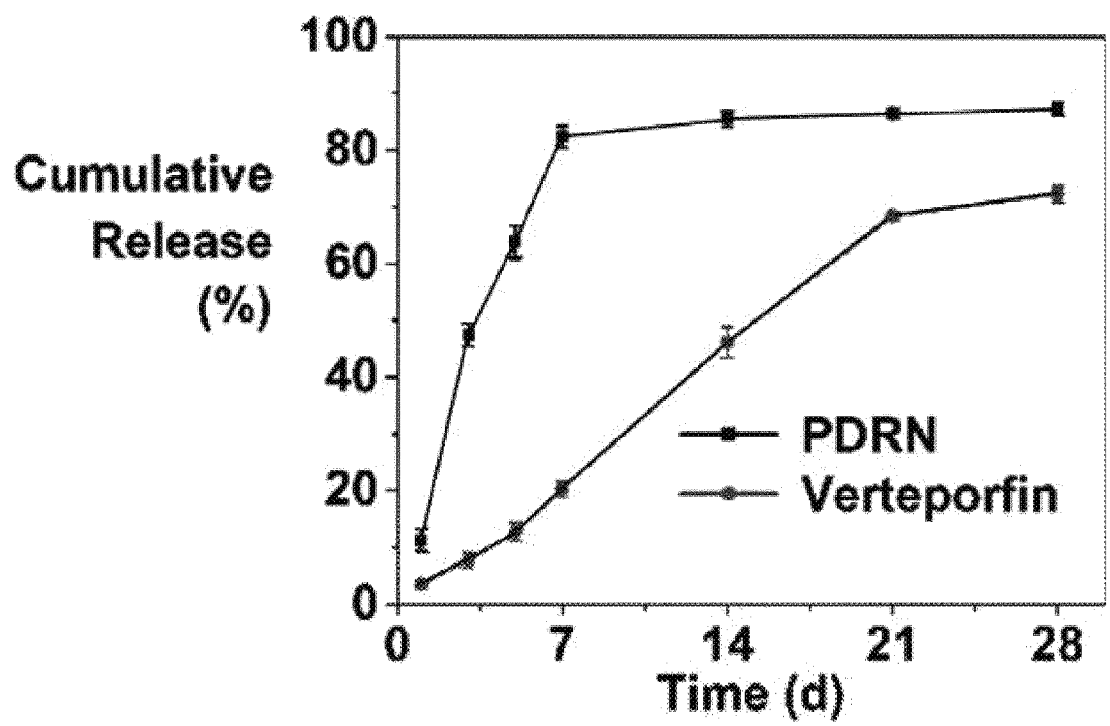
FIG. 4H shows the cumulative release of PDRN and verteporfin in PBS at 37° C.

4B shows a TEM image of the drug-loaded micelles (with a scale of 500 nm), showing that the PLGA-PEG-NB/verteporfin micelles have a uniform spherical shape; FIG. 4C shows the size distribution of the drug-loaded micelles, determined by hydrodynamic diameter measurement, the micelles are dissolved in PBS solution at pH 7.4, the average particle size measured is 79.9 nm; FIG. 4D shows the mechanical properties of SQPV hydrogels at different polymer and micelle concentrations, showing that the storage modulus of the hydrogels is significantly increased by increasing the levels of QCSG/SFMA polymer and PLGA-PEG-NB micelles; FIG. 4E shows the general transparency observation of SQPV hydrogels at different micelle concentrations, and the transmittance analysis reveals that 1 mm thick SQPV hydrogel sheets become opaque when the concentration of PLGA-PEG-NB micelles reaches 1 wt %; it is notable that the SQPV hydrogel consisting of 9% QCSG/SFMA polymer and 0.5% PLGA-PEG-NB micelles has a storage modulus of 4 kilopascals (KPa), which approximates the storage modulus of native cornea and meets the transparency criteria for keratoprostheses, which is proved to be the optimal corneal substitute; FIG. 4F shows an SEM image (scale of 10 micrometers (μm)) of the SQPV hydrogel, indicating that the SQPV hydrogel displays an interconnected porous microstructure, with an average pore size of 41.03±0.21 μm, and this porous and interconnected structure not only facilitates the regulation of cell growth, attachment, and proliferation, but also strongly supports the secretion of extracellular matrix (ECM); the porous nature of SQPV hydrogels also facilitates a two-stage drug release pattern resulting from different drug delivery mechanisms, specifically, the hydrophilic drug PDRN is dispersed in the SQPV hydrogel backbone, while the hydrophobic drug verteporfin remains encapsulated in PLGA-PEG-NB micelles; FIG. 4G shows a histogram of the porosity and pore size of the SQPV hydrogel based on SEM data, n=3, indicating a greater hydrophilicity of the free PDRN and a faster release rate than that of verteporfin; FIG. 4H shows the cumulative release of PDRN and verteporfin in PBS at 37° C., and the curves indicate that almost all encapsulated PDRN is released within 7 days, in contrast, verteporfin is released significantly slower from the SQPV hydrogel, with only 72% released after 28 days of incubation, suggesting that the ability of the SQPV hydrogel to control drug delivery both spatiotemporally and sequentially is a key advantage for corneal repair.

Comparative Embodiment 1

Preparation of SQP Hydrogel:
Compared with Embodiment 1, the only difference is that the addition of verteporfin is omitted.

Comparative Embodiment 2

Preparation of SQ Hydrogel:
Compared with Embodiment 1, the only difference is that the addition of PDRN and verteporfin is omitted.

Embodiment 2

The antibacterial properties of SQPV hydrogel prepared in Embodiment 1, SQP hydrogel prepared in Comparative embodiment 1 and SQ hydrogel prepared in Comparative embodiment 2 are investigated, and the antibacterial effects of SQPV hydrogel on Gram-positive methicillin-resistant *Staphylococcus aureus* (MRSA) and Gram-negative multi-drug-resistant *Pseudomonas aeruginosa* (MRPA) are evaluated.

Quantitative analysis is carried out on Luria-Bertani (LB) agar plate. The inoculation amount of bacteria is $1*10^7$ CFU/mL, the addition amount of hydrogel is 200 μL, and the control group is gel without water.

Figure 5A:
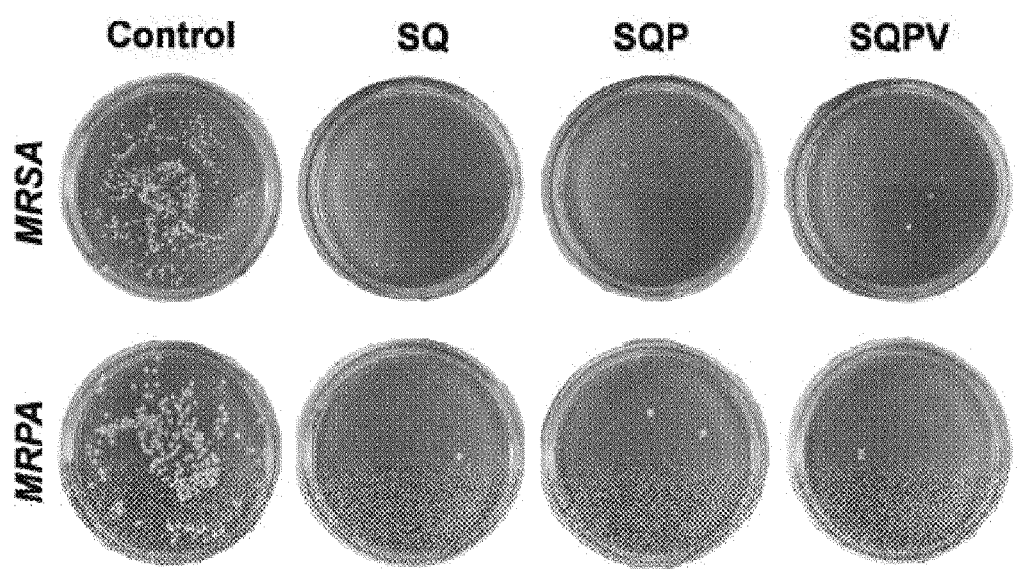
FIG. 5A is the colony image of SQ (abbreviation of SFMA and QCSG), SQP (Abbreviation for polymer after SFMA, QCSG loading PDRN) and SQPV hydrogel on Luria-Bertani (LB) agar plate.
Figure 5B:
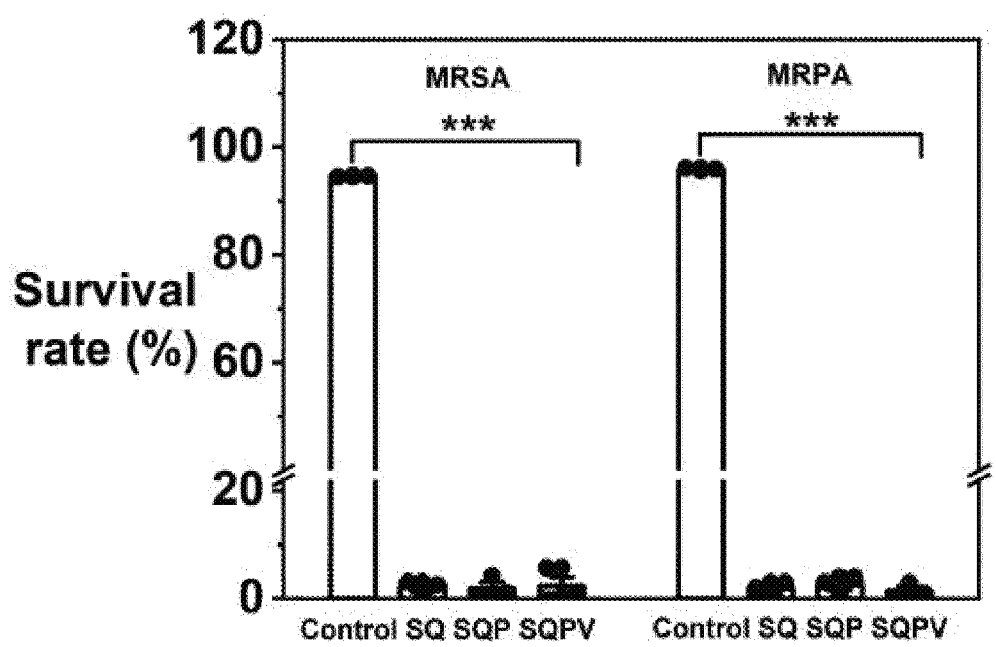
FIG. 5B is the quantitative statistical histogram of the corresponding bacterial survival rate.
Figure 5C:
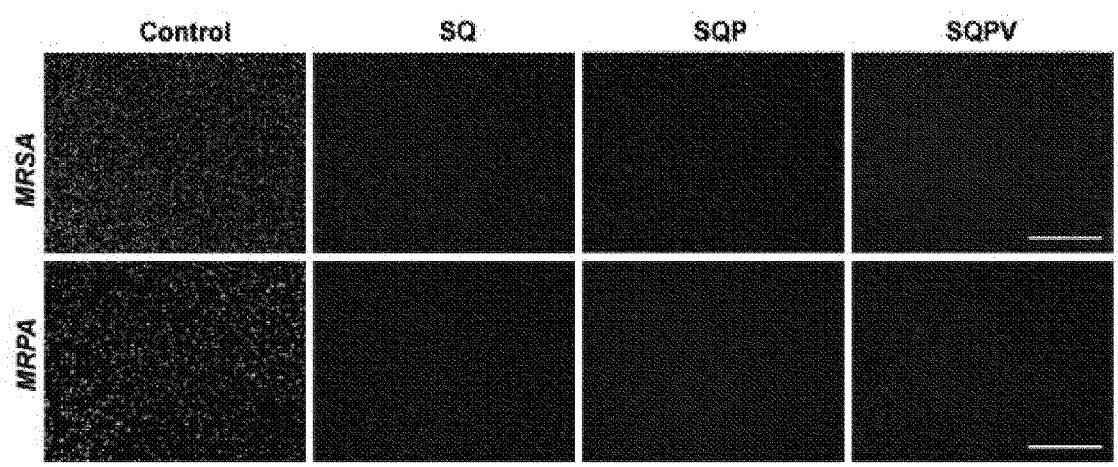
FIG. 5C is the live/dead staining diagram of Methicillin-resistant Staphylococcus aureus (MRSA) and (multidrug-resistant Pseudomonas aeruginosa) MRPA co-cultured with SQ, SQP and SQPV hydrogels.
Figure 5D:
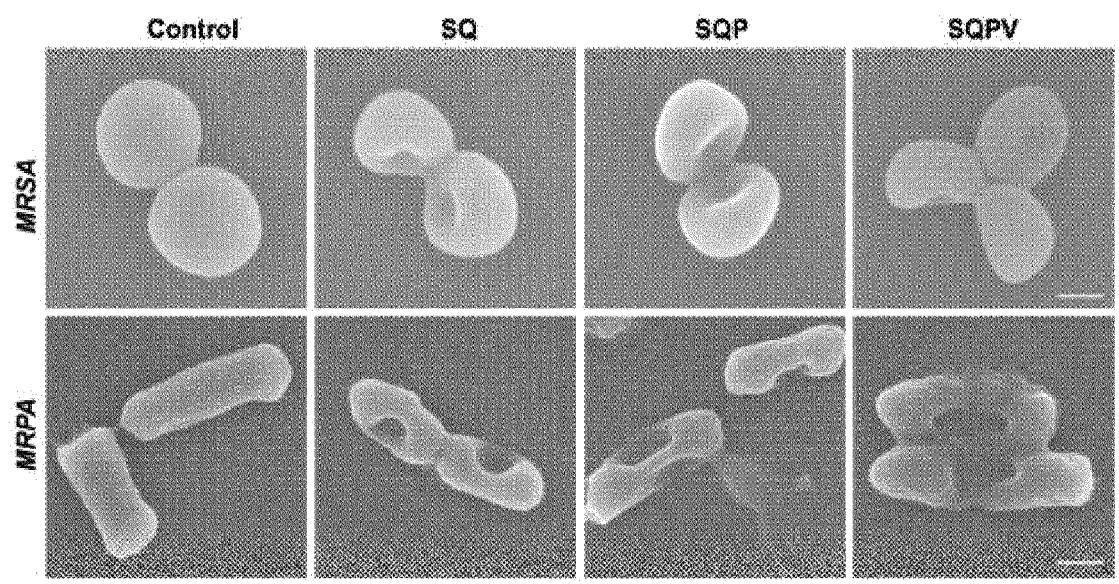
FIG. 5D is the SEM image of MRSA and MRPA co-cultured with SQ, SQP and SQPV hydrogels.

The results are shown in FIG. 5A-FIG. 5D. The images of colonies of SQ, SQP and SQPV hydrogels on LB agar plates are shown in FIG. 5A; compared with the control group, there are few colonies in SQ, SQP and SQPV hydrogel treatment groups; FIG. 5B shows the corresponding quantitative statistical histograms of bacterial survival (data represent mean±SD, n=3, *p<0.05, p<0.01, *p<0.001), and quantitative analyses of bacterial colony counts confirms that more than 99% of MRSA and MRPA are eradicated by QCSG-based hydrogels, which is attributed to the cationic effect of QCSG in the hydrogels; the live/dead staining plots of MRSA and MRPA after co-culture with SQ, SQP and SQPV hydrogels are shown in FIG. 5C; the results of the live/dead staining test show that the bacteria in the control group exhibit green fluorescence, whereas the hydrogel-treated bacteria display obvious red fluorescence with negligible green fluorescence, indicating that the QCSG-based hydrogel has a significant bactericidal effect; SEM images of MRSA and MRPA after co-culture with SQ, SQP and SQPV hydrogels (scale of 200 nm) are shown in FIG. 5D; the SEM images shows the morphological changes of MRSA and MRPA after QCSG-based hydrogel treatment, the bacteria in the control group have maintained their smooth and undamaged cell membranes, in contrast, the bacteria treated with QCSG hydrogel shows significant damage to their cell walls and cell membranes, which proves that the QCSG hydrogel has a strong antimicrobial capacity.

Embodiment 3

The anti-inflammatory properties of SQPV hydrogel prepared in Embodiment 1, SQP hydrogel prepared in Comparative embodiment 1 and SQ hydrogel prepared in Comparative embodiment 2 are investigated. The complex pathophysiology of inflammatory reaction after corneal transplantation significantly affects the postoperative microenvironment. Therefore, regulating inflammatory response has become the key focus of developing ideal corneal substitutes. Macrophages are the predominant immune cells at the post-transplant wound site, exhibiting heterogeneity and plasticity, polarized to an M1 pro-inflammatory or M2 anti-inflammatory phenotype.

In this present disclosure, Raw264.7 cells are inoculated on a 6-well plate for 24 h, and then stimulated with LPS (100 nanograms per milliliter (ng/mL)) and interferon gamma (IFN-γ) (20 ng/mL) for 24 h to induce M1 polarization. Then, fresh hydrogel leaching solution is added, and after 24 h, the cytoskeleton is stained with CLSM to observe the morphological changes of macrophages.

Figure 6:
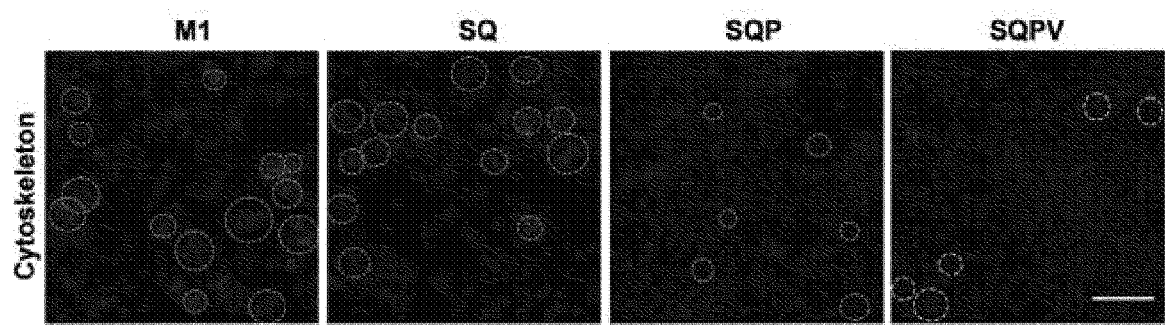
FIG. 6 is a staining diagram of macrophage cytoskeleton treated with SQPV hydrogel, SQP hydrogel and SQ hydrogel.

It is demonstrated by macrophage cytoskeleton staining that PDRN promotes macrophages to have M1 to M2 transformation, and the results are shown in FIG. 6, where SQP and SQPV hydrogel-treated macrophages are changed from spindle shaped with multiple pseudopods to rounded, indicating the activation of M2 polarization in the M1-phenotyped macrophages.

Embodiment 4

The in vivo biocompatibility of SQPV hydrogel prepared in Embodiment 1, SQP hydrogel prepared in Comparative embodiment 1 and SQ hydrogel prepared in Comparative embodiment 2 is evaluated.

Biocompatibility is the key factor for SQPV hydrogel to promote cell proliferation and migration, thus accelerating corneal wound healing. In order to prove that SQPV hydrogel has good cell compatibility and minimal biological toxicity, the present disclosure carries out cell life and death staining on corneal epithelial cells and corneal stromal cells.

Methods: HCEC or HCSC cells are inoculated in 24-well culture plates at a density of $1\times10^5$ cells per well and incubated for 24 h at 37° C. in a 5% $CO_2$ atmosphere. Subsequently, fresh hydrogel leaching solution is used to replace the original culture solution. After incubation for 24 h, the cells are stained with calcein-AM/PI dye and imaged by fluorescence microscope.

Figure 7A:
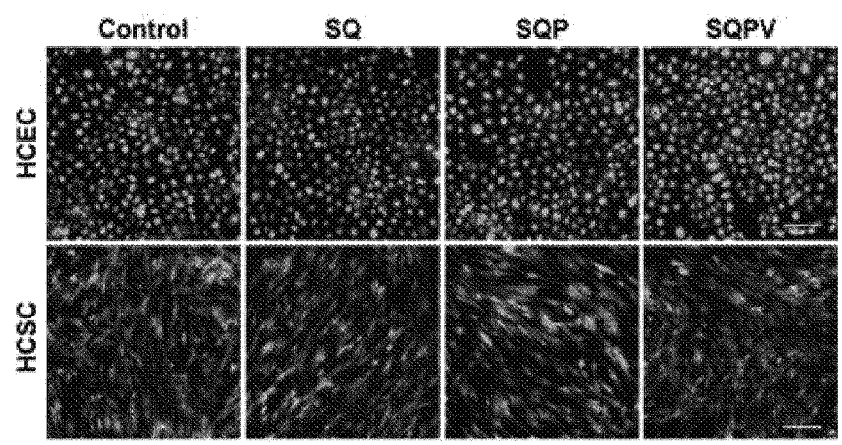
FIG. 7A is the live/dead staining image of human corneal endothelial cells (HCEC) and Human corneal stromal cells (HCSC) after being treated with SQ, SQP and SQPV hydrogel lixivium for 24 h.
Figure 7B:
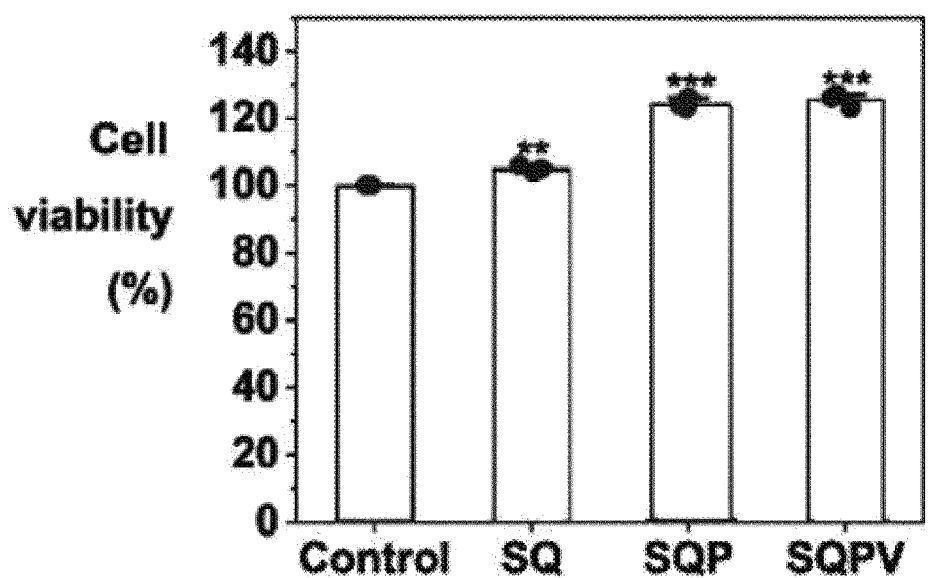
FIG. 7B illustrates the cell viability of HCEC cells treated with different hydrogels.
Figure 7C:
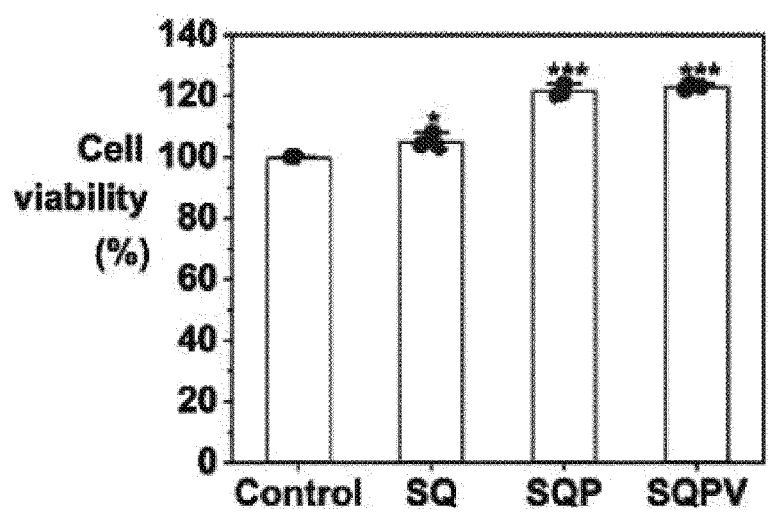
FIG. 7C shows the cell viability of HCSC cells treated with different hydrogels.
Figure 7D:
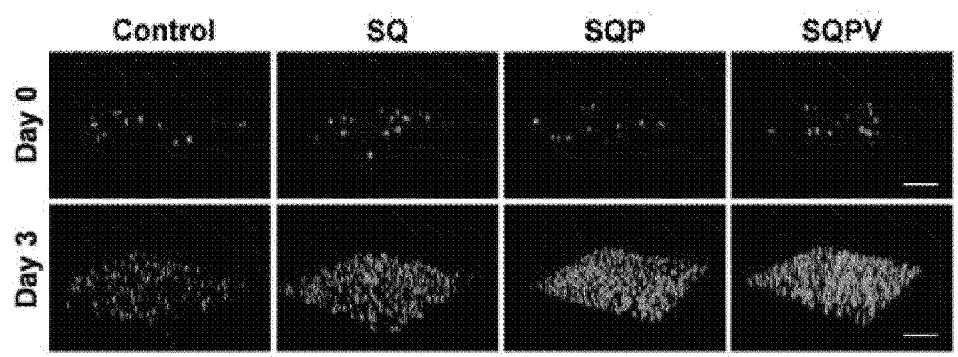
FIG. 7D is the confocal laser scanning microscopy (CLSM) image of HCSC cells encapsulated in different hydrogels after 3 days of culture.

The results are shown in FIG. 7A-FIG. 7D. FIG. 7A shows live/dead staining images (scale of 100 μm) of HCEC and HCSC cells after treatment with SQ, SQP and SQPV hydrogel leachate for 24 h. It shows that strong green fluorescence and negligible red fluorescence are observed in HCEC and HCSC cells after treatment with SQ, SQP and SQPV hydrogels for 24 h, thus confirming that the prepared hydrogels have a good biocompatibility; the cytotoxicity of SQPV hydrogel-treated HCEC and HCSC cells is assessed using Cell Counting Kit-8 (CCK-8); FIG. 7B shows the cell viability of HCEC cells treated with different hydrogels; FIG. 7C illustrates the cell viability of HCSC cells treated with different hydrogels; the results show that both SQP and SQPV hydrogel treatment groups show higher cell viability than the control group and SQ hydrogel group, which indicates that the cytotoxicity of SQPV hydrogel may be ignored; FIG. 7D is the CLSM image (scale of 500 μm) of HCSC cells encapsulated in different hydrogels after 3 days of culture; the proliferative effects of SQPV hydrogels on HCSC are investigated by using 3D incubation mode, and it is observed from the confocal microscopy that the sustained proliferation of HCSC in hydrogels is observed with the increase of incubation time.

Embodiment 5

The fibrotic attenuation capability of SQPV hydrogel prepared in Embodiment 1, SQP hydrogel prepared in Comparative embodiment 1 and SQ hydrogel prepared in Comparative embodiment 2 is investigated.

The expression levels of YAP1, α-SMA and COL-IA in HCSC are detected by immunofluorescence. Firstly, HCSC cells are co-cultured with different hydrogel extracts for 24 h to make the cells adhere to the cell wall. Then the cells are washed twice with PBS, fixed with 4% paraformaldehyde, permeated with 0.1% Triton and sealed with 5% BSA. The cells are then incubated with the primary antibody, then with the corresponding secondary antibody and DAPI, and finally observed under a microscope. In RT-PCR analysis, the total RNA in HCSC is extracted by using nuclear RNA kit, and then reverse transcribed into cDNA by using HiScript III RT SuperMix kit. Quantitative PCR is performed with SYBR Green reagent. The cycle condition is 95° C. for 10 seconds(s), followed by 40 two-step cycles (95° C. for 15 s and 60° C. for 30 s). The quantitative data with β-actin as internal control are analyzed by sequence detection system software.

Figure 8A:
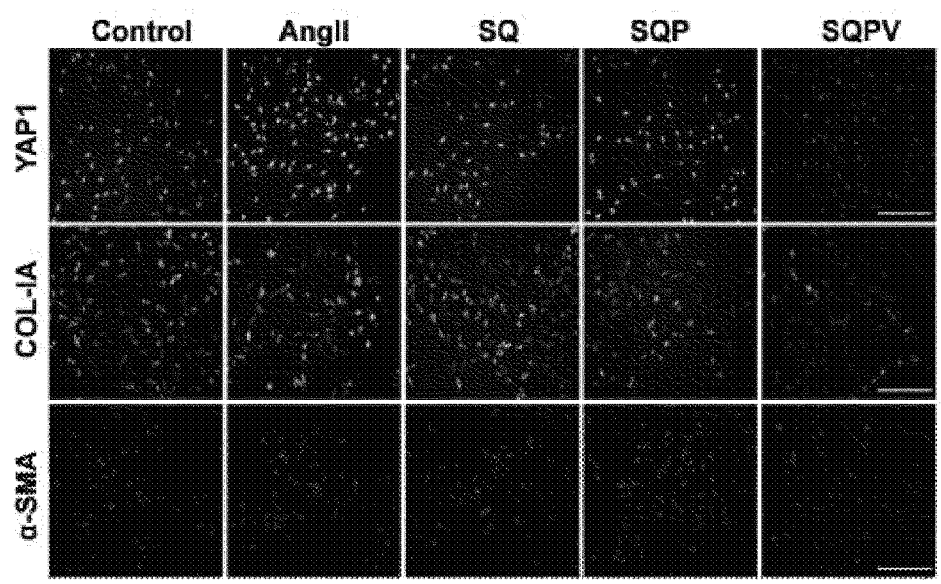
FIG. 8A shows the CLSM analysis results of the fibrosis attenuation ability of SQPV hydrogel, SQP hydrogel and SQ hydrogel.
Figure 8B:
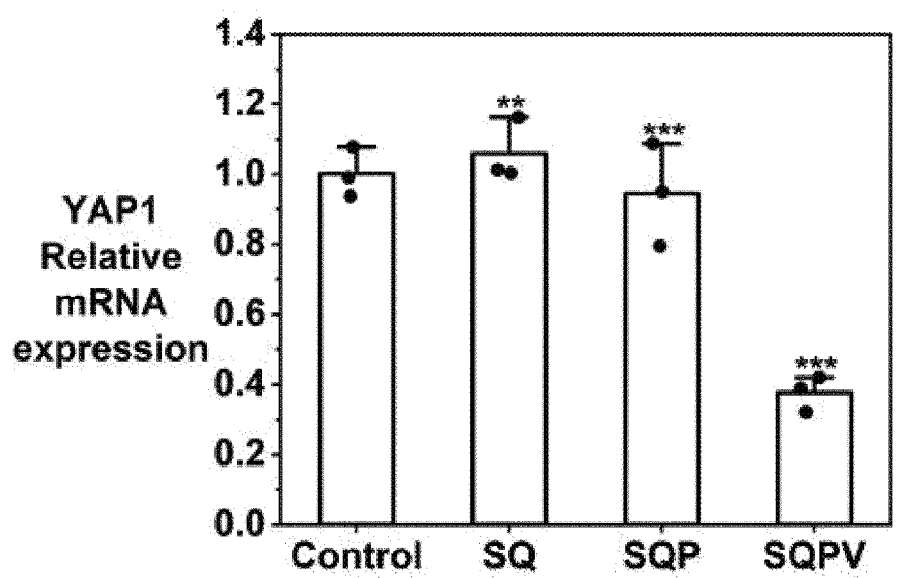
FIG. 8B shows the results of reverse transcription polymerase chain reaction (RT-PCR) analysis of yes-associated protein 1 (YAP1).
Figure 8C:
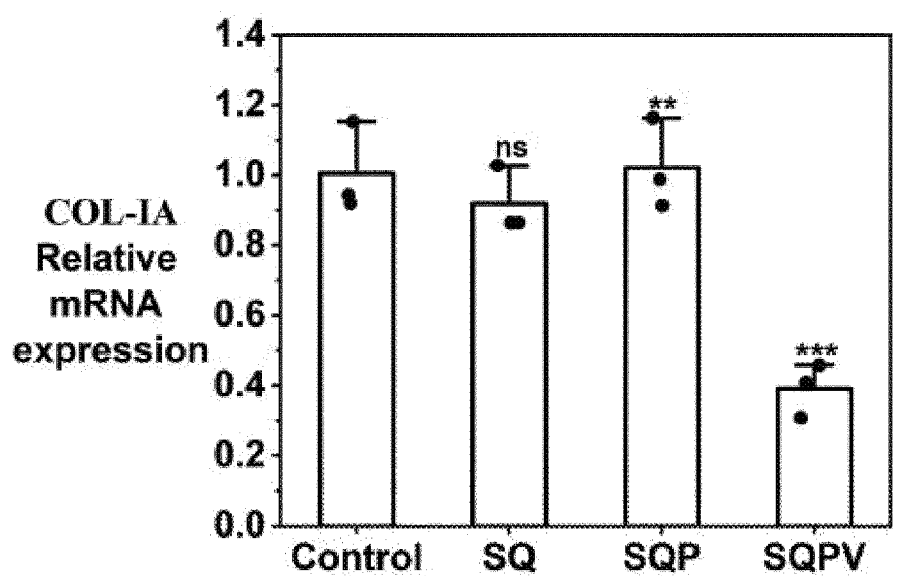
FIG. 8C shows the results of RT-PCR analysis of collagen type I alpha (COL-IA).
Figure 8D:
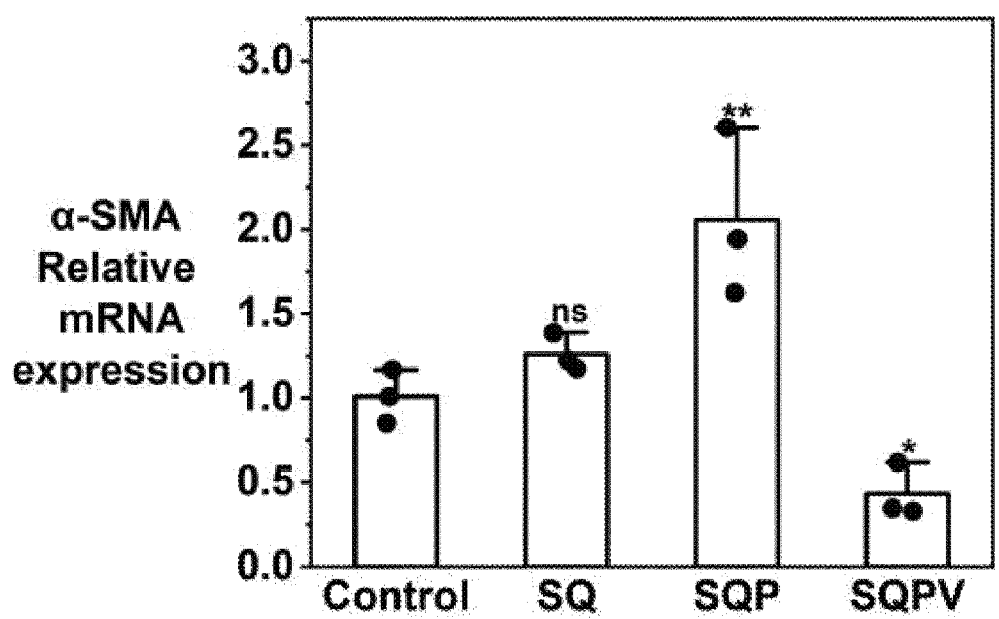
FIG. 8D shows the RT-PCR analysis result of alpha-smooth muscle actin (α-SMA).

In order to prove the antibacterial ability of SQPV hydrogel, immunofluorescence staining of corneal stromal cells is carried out according to the present disclosure, and the results are shown in FIG. 8A-FIG. 8D. FIG. 8A is the result of CLSM analysis (the scale is 60 μm), which shows that compared with the control group, SQP group and SQP treatment group, the expression level of YAP1 in HCSC cells treated with SQPV hydrogel is decreased, and alpha-smooth muscle actin (α-SMA) and collagen type I alpha (COL-IA) around HCSC cells are decreased. FIG. 8B shows the results of RT-PCR analysis of YAP1 (n=3), FIG. 8C shows the results of RT-PCR analysis of COL-IA (n=3), and FIG. 8D shows the results of RT-PCR analysis of α-SMA (n=3). RT-PCR results suggest that the expression levels of YAP1, COL-IA and α-SMA in SQPV hydrogel treatment group are decreased, which is consistent with that of CLSM analysis.

Embodiment 6

The SQPV hydrogel prepared in Embodiment 1, SQP hydrogel prepared in Comparative embodiment 1 and SQ hydrogel prepared in Comparative embodiment 2 are evaluated for corneal wound healing in vivo.

In order to evaluate the effect of SQPV hydrogel on corneal wound healing in vivo, a corneal wound infection model is established using New Zealand rabbits after lamellar keratectomy. The animal model is established as follows: 30 New Zealand white rabbits weighing 3 kg are selected; the rabbits are generally anesthetized by intravenous injection of 2% pentobarbital sodium (40-50 mg/kg) and local injection of 0.5% propacaine hydrochloride eye drops. Subsequently, a 3.5 mm trephine (about ⅓ of the corneal depth) is used to partially trephine (cut) the center of the right cornea of each rabbit. A sterile cotton swab is dipped into a prepared $1\times10^8$ Pseudomonas aeruginosa bacterial load and dropped evenly onto the rabbit corneal defect wound. Then, 10 μL of hydrogel disinfection prepolymer solution is injected into the defect site with a micropipette and gelled with visible light for 1 min. Rabbit eyes subjected only to corneal defect surgery are coated with bacteria in which no hydrogel is placed to serve as a control group. The rabbit eyes are evaluated immediately after surgery (day 0) using slit lamp microscopy and anterior segment optical coherence tomography. The lamellar transplantation model is thus constructed.

Figure 9A:
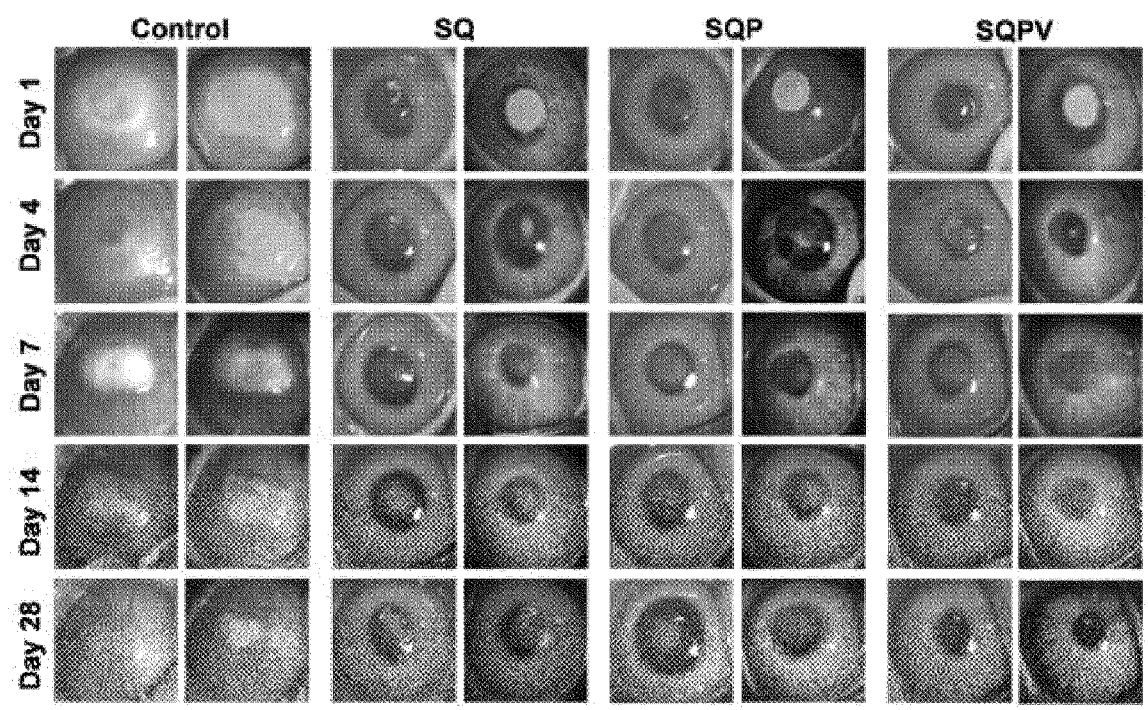
FIG. 9A is the slit lamp photograph and cobalt blue fluorescence staining from the first day to the 28th day of corneal transplantation.
Figure 9B:
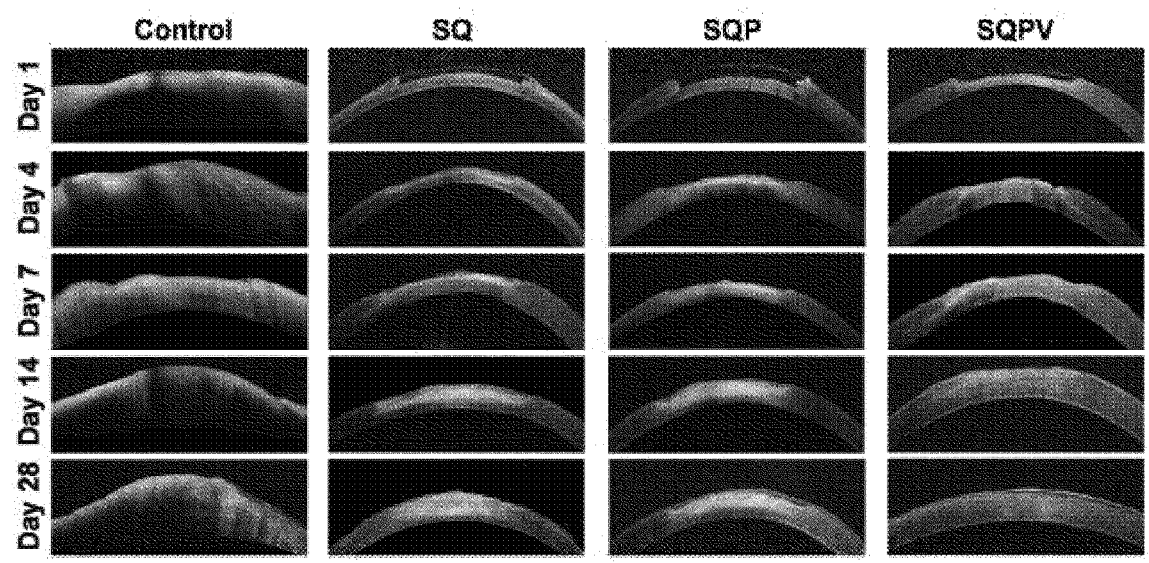
FIG. 9B is an anterior segment optical coherence tomography (AS-OCT) image.

The results of slit-lamp images, cobalt blue fluorescence staining and AS-OCT images are shown in FIG. 9A and FIG. 9B, where FIG. 9A is slit-lamp images and cobalt blue fluorescence staining from the first day to the 28th day of corneal transplantation, and FIG. 9B is AS-OCT image. The slit lamp image shows that there is almost no bacterial infection in SQ, SQP and SQPV hydrogel treatment groups compared with the control group, which verifies the antibacterial effect of hydrogels in vivo. The wounds treated with SQP and SQPV hydrogels are completely re-epithelialized within 4 days, while the epithelial defects in the control group still exist even after 28 days, which indicate that SQP and SQPV hydrogels may accelerate the re-epithelialization of wounds. AS-OCT images taken on the 28th day suggest that compared with the control group, interstitial tissue and newly formed corneal epithelium in all hydrogel treatment groups are dense.

Figure 10A:
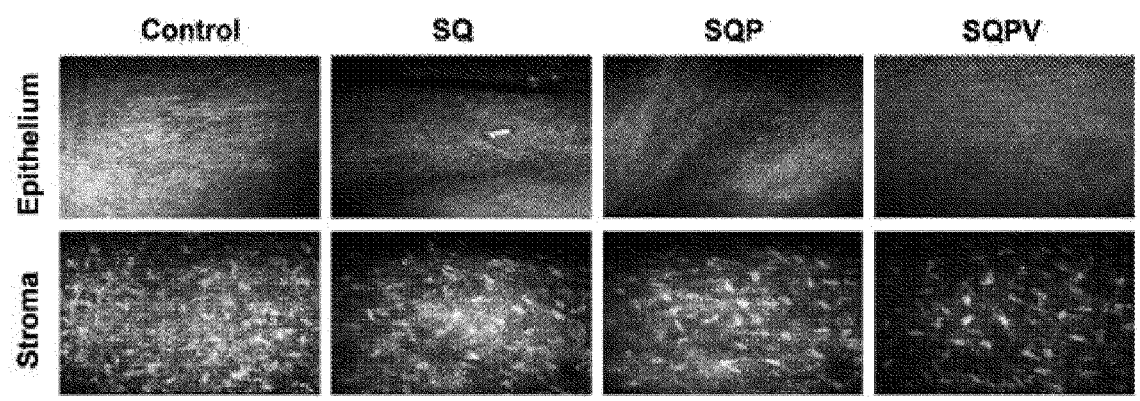
FIG. 10A is the confocal micrograph of corneal epithelium and corneal stroma of rabbits after 28 days of operation.
Figure 10B:
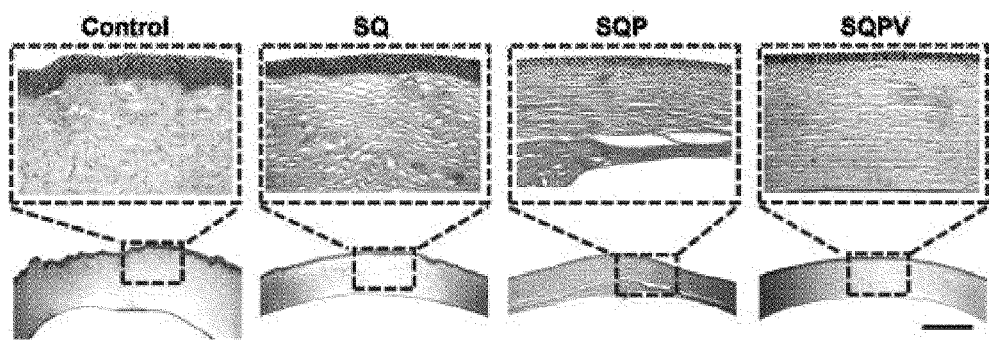
FIG. 10B is the hematoxylin and eosin (H&E) staining image of cornea treated with different hydrogels on the 28th day after operation.

The results of CLSM analysis and H&E staining images on 28th day are shown in FIG. 10A and FIG. 10B, where FIG. 10A is the confocal micrograph of corneal epithelium and corneal stroma after 28 days of operation (with scale of 50 μm), and FIG. 10B is the H&E staining image of cornea after 28 days of operation treated with different hydrogels (with scale of 50 μm). CLSM images indicate that the regenerated epithelial cells and matrix in hydrogel treatment group are more organized than those in control group (FIG. 10A), which further reveal the superior function of SQPV hydrogel in promoting corneal wound healing. Histopathological evaluation by H&E staining suggests that the cornea treated by SQPV shows similar optical reflectivity and structural characteristics to the original cornea after 28 days of treatment, while the corneas in other groups show visible scars in the pupil area (FIG. 10B).

The anti-infection, anti-inflammation, proliferation and remodeling stages of SQPV hydrogel prepared in Embodiment 1, SQP hydrogel prepared in Comparative embodiment 1 and SQ hydrogel prepared in Comparative embodiment 2 are comprehensively evaluated.

Figure 11A:
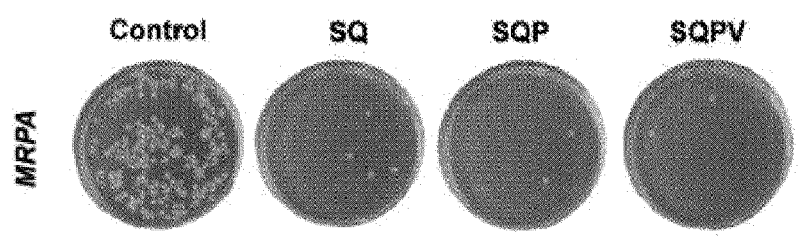
FIG. 11A is the colony photo of corneal tissue on LB agar plate after hydrogel treatment for 1 day.
Figure 11B:
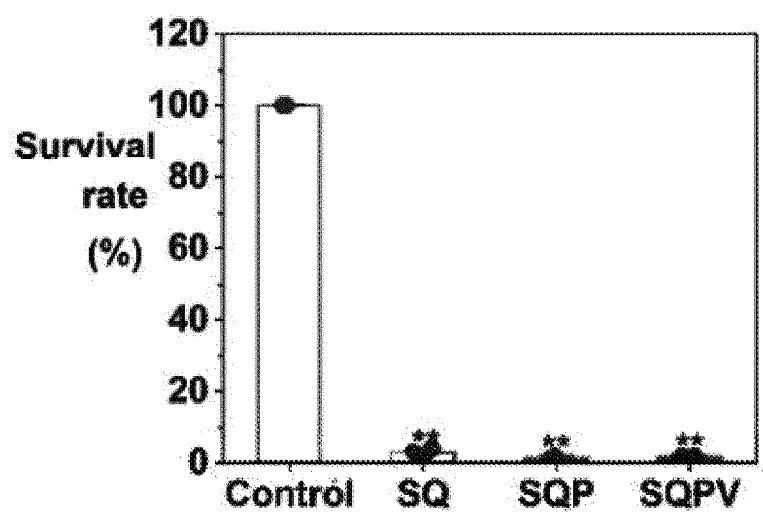
FIG. 11B is the corresponding quantitative result of viable bacteria.

In order to evaluate the antibacterial function of hydrogel, the corneal tissue treated with hydrogel for 1 day is collected, and the colony photos of it on LB agar plate are shown in FIG. 11A, and the corresponding quantitative results of viable bacteria in cornea after different treatments are shown in FIG. 11B. The results of bacterial quantitative detection show that the CFU of hydrogel treatment group is obviously less than that of control group, which is because QCSG shows positive charge effect in hydrogel, indicating that hydrogel has strong antibacterial effect in vivo.

Figure 12A:
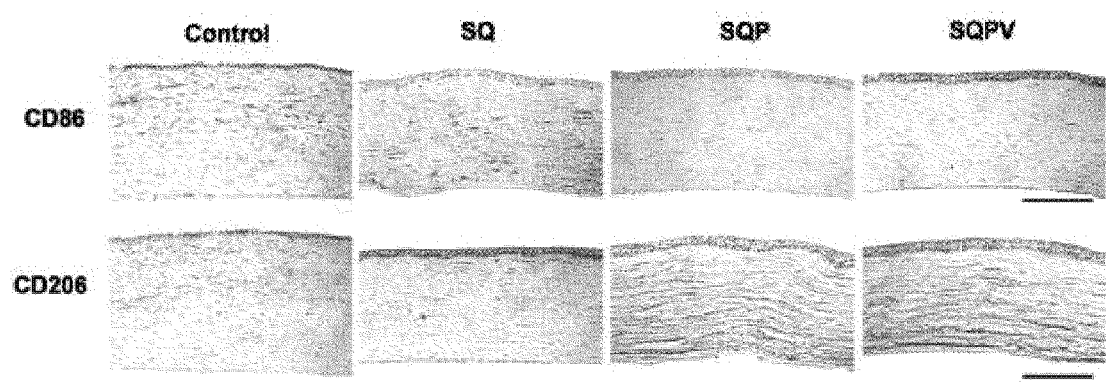
FIG. 12A shows the immunohistochemical staining of CD86 and CD206 in cornea on the 4th day.
Figure 12B:
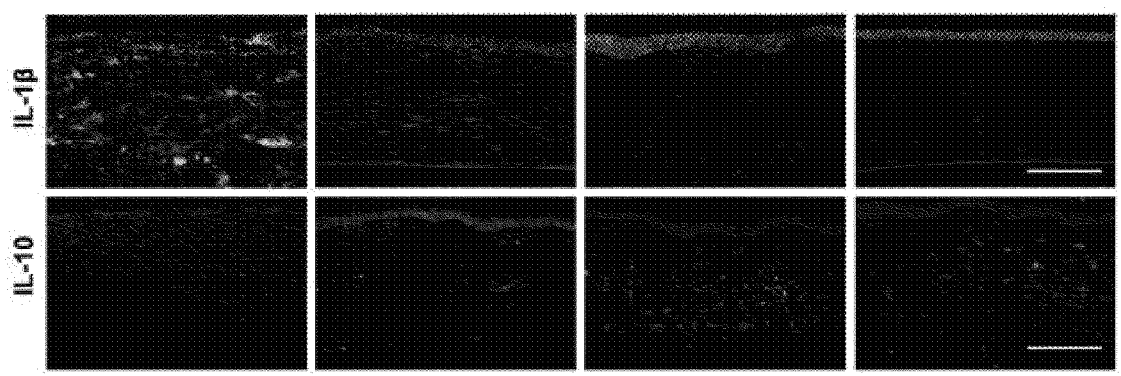
FIG. 12B is the immunofluorescence staining image of IL-10 and IL-1β.
Figure 12C:
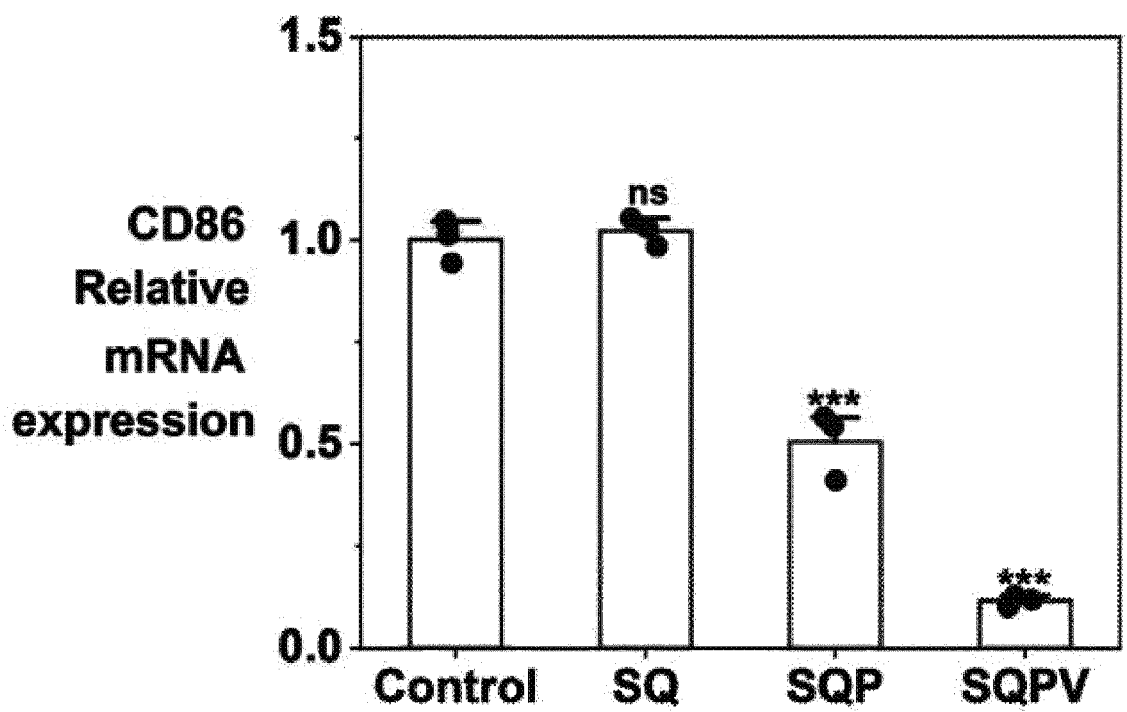
FIG. 12C is the result of RT-PCR analysis of CD86.
Figure 12D:
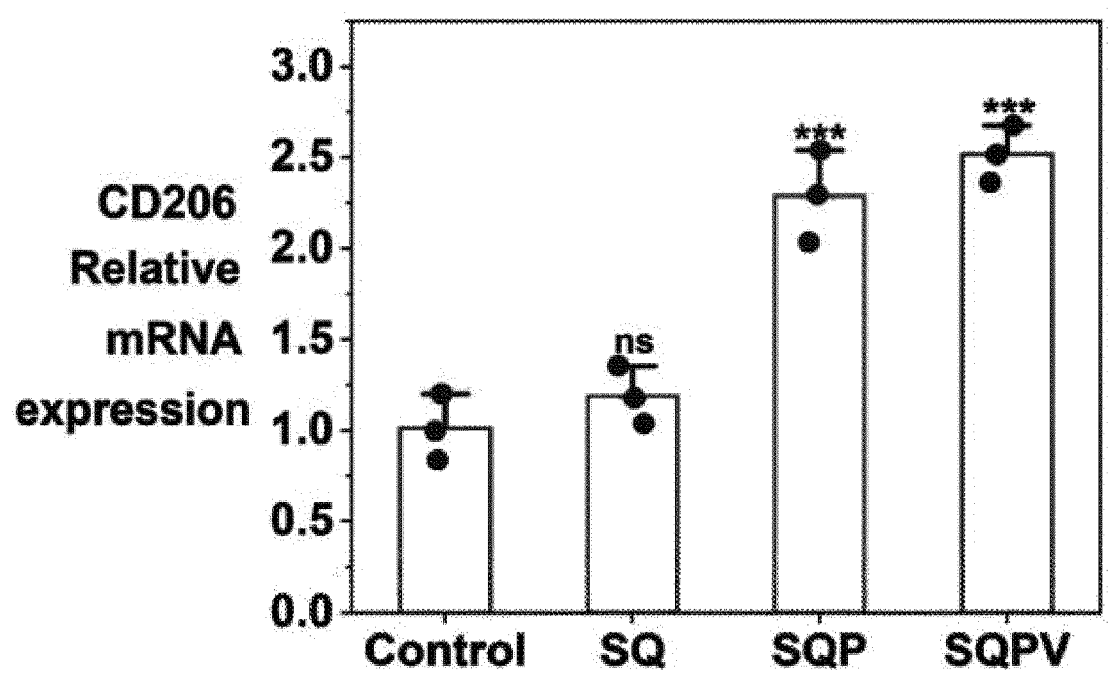
FIG. 12D is the result of RT-PCR analysis of CD206.
Figure 12E:
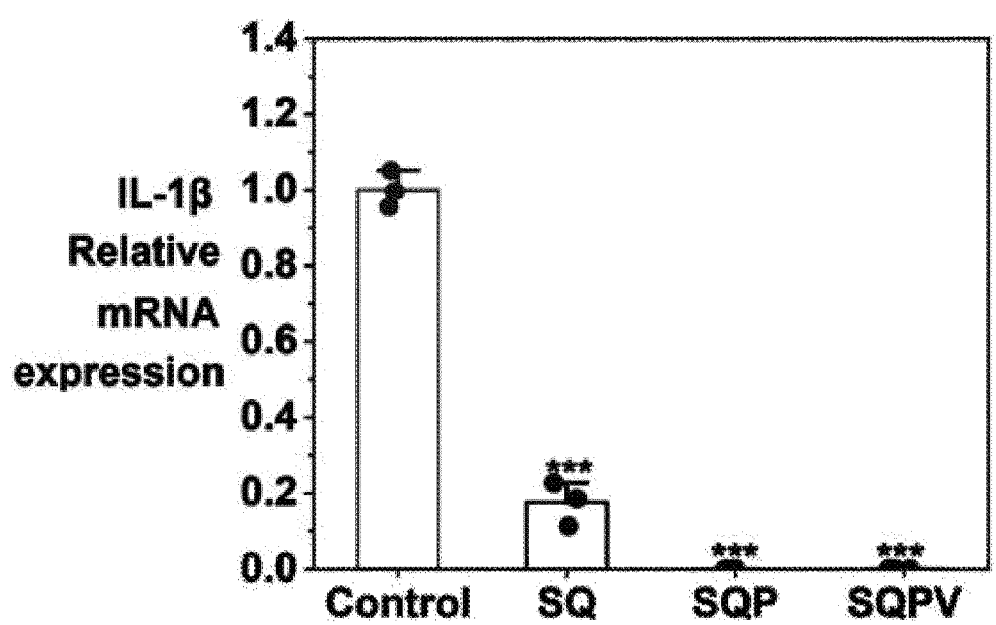
FIG. 12E is the result of RT-PCR analysis of IL-1β.
Figure 12F:
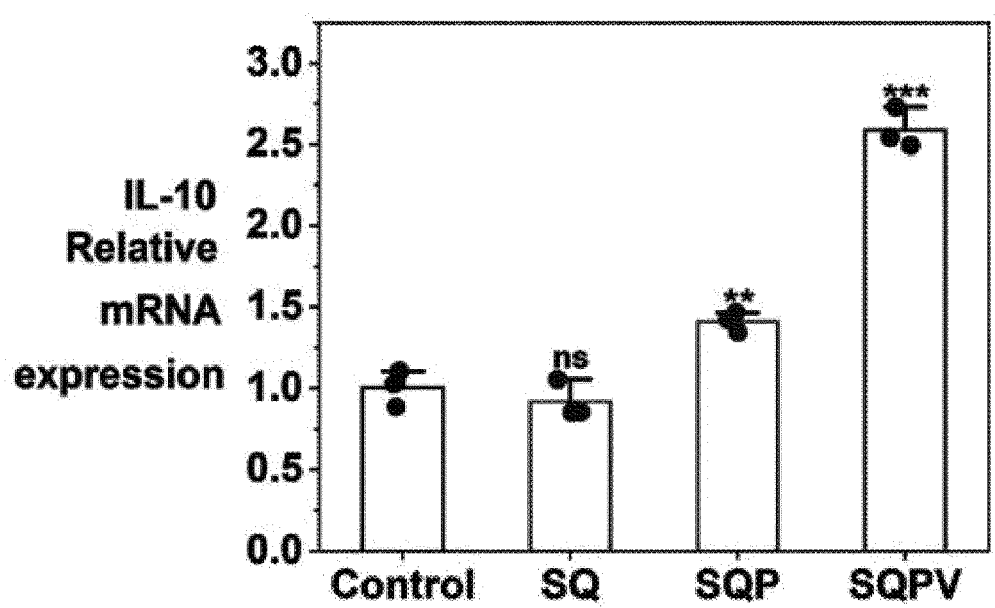
FIG. 12F is the result of RT-PCR analysis of IL-10.

To assess the effect of SQPV hydrogel on the regulation of this phase, the polarization of trabecular macrophages is analyzed by immunohistochemical staining in rabbits at 4 days postoperatively. The results are shown in FIG. 12A-FIG. 12F, where FIG. 12A is CD86 and CD206 (scale of 20 μm) in corneal tissue 4 days after operation; FIG. 12B is IL-1β and IL-10 (scale of 60 μm) in corneal tissue 4 days after operation; FIG. 12C shows the PCR quantitative results of CD86; FIG. 12D shows the PCR quantitative results of CD206; FIG. 12E shows the PCR quantitative results of IL-1β; and FIG. 12F shows the PCR quantitative results of IL-10.

The results suggest that after treatment with SQP and SQPV hydrogels, the expression of CD86 (M1 phenotype) is decreased significantly, while the expressions of CD206 (M2 phenotype) and CD206 (M2 phenotype) are increased significantly, indicating that these hydrogels promote the transformation of pro-inflammatory M1 macrophages into anti-inflammatory M2 macrophages (FIG. 12A). The consistent expression trend of pro-inflammatory factor IL-1β and anti-inflammatory factor IL-10 further confirms these results, which may be due to the release of PDRN in SQP and SQPV hydrogel treatment groups (FIG. 12B). The mRNA levels of M1 cytokines (CD86, IL-1β) and M2 cytokines (CD206, IL-10) are detected by RT-PCR. In the PDRN-loaded hydrogel treatment group, it may be clearly observed that the level of M1 cytokine mRNA is down-regulated and the level of M2 cytokine mRNA is up-regulated (FIG. 12C-FIG. 12F).

Growth factors play a key role in cell proliferation, driving processes such as corneal stromal keratinocyte activation, muscle differentiation and ECM formation. The present disclosure carries out immunohistochemical staining on transforming growth factor (TGF-β1) and platelet-derived growth factor (PDGF) to evaluate the expression of growth factors 7 days after operation.

Figure 13A:
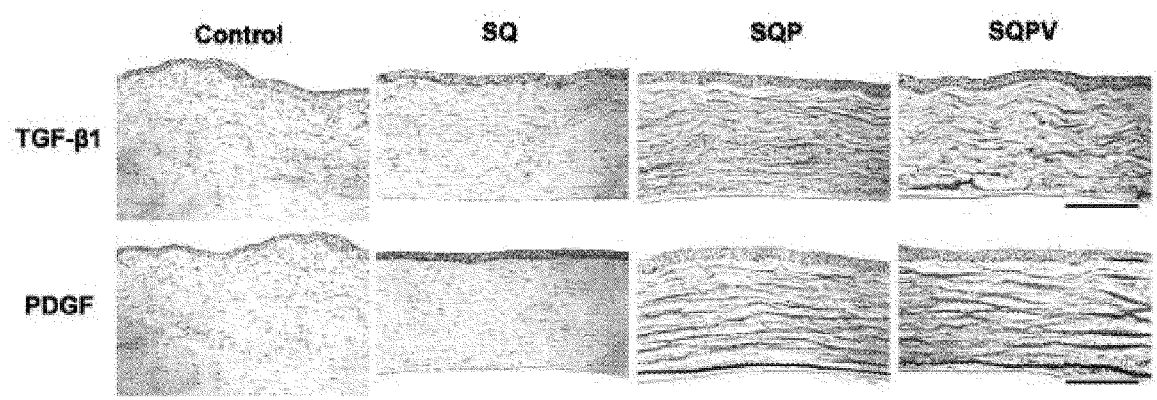
FIG. 13A shows the immunohistochemical staining of transforming growth factor-beta1 (TGF-β1) and platelet derived growth factor (PDGF) in cornea on the 7th day.
Figure 13B:
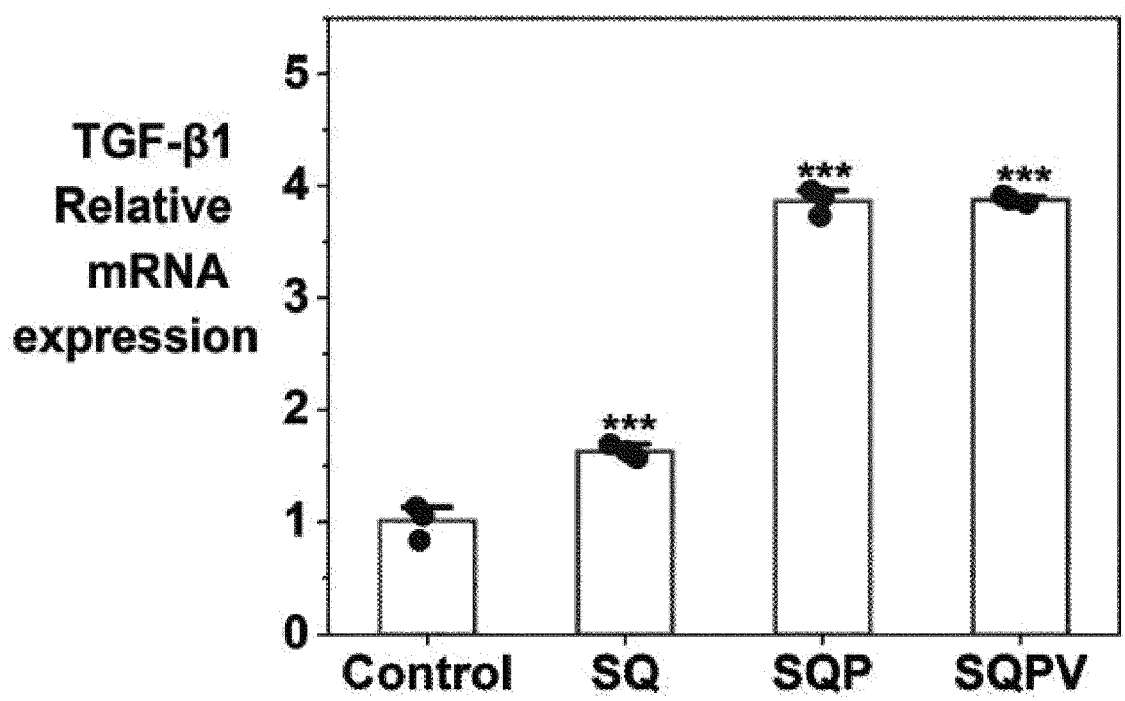
FIG. 13B is the result of RT-PCR analysis of TGF-β1.
Figure 13C:
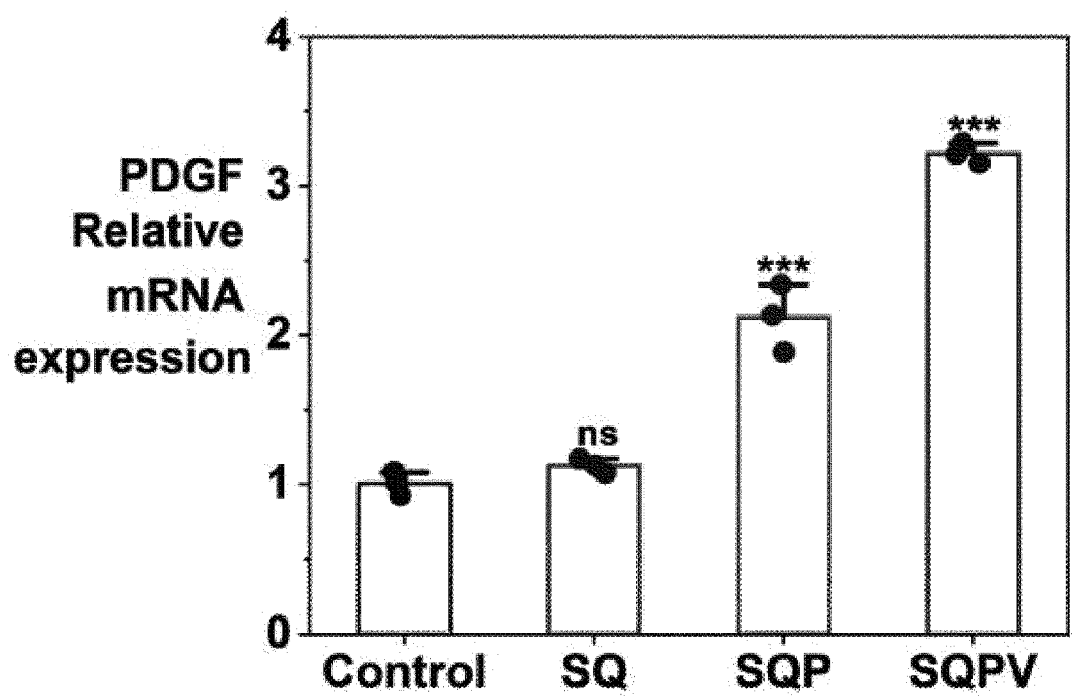
FIG. 13C is the result of RT-PCR analysis of PDGF.

The results are shown in FIG. 13A-FIG. 13C, where FIG. 13A is the immunofluorescence staining chart of TGF-β1 and PDGF in cornea on the 7th day (scale of 20 μm); FIG. 13B shows the results of RT-PCR analysis of TGF-β1; FIG. 13C shows the results of RT-PCR analysis of PDGF. FIG. 13A-FIG. 13C shows that compared with SQP group and control group, the expression levels of all types of growth factors in SQPV and SQP treatment groups are the most significant. Quantitative analysis further shows that the relative expression levels of TGF-β1 and PDGF in SQPV and SQP treatment groups are higher than those in SQ treatment group and control group.

In the remodeling stage of corneal wound healing, the formation of scar may have an adverse effect on the final visual outcome. Therefore, the capability of SQPV hydrogel to regulate the corneal wound healing and remodeling stage is evaluated in the present disclosure.

Figure 14A:
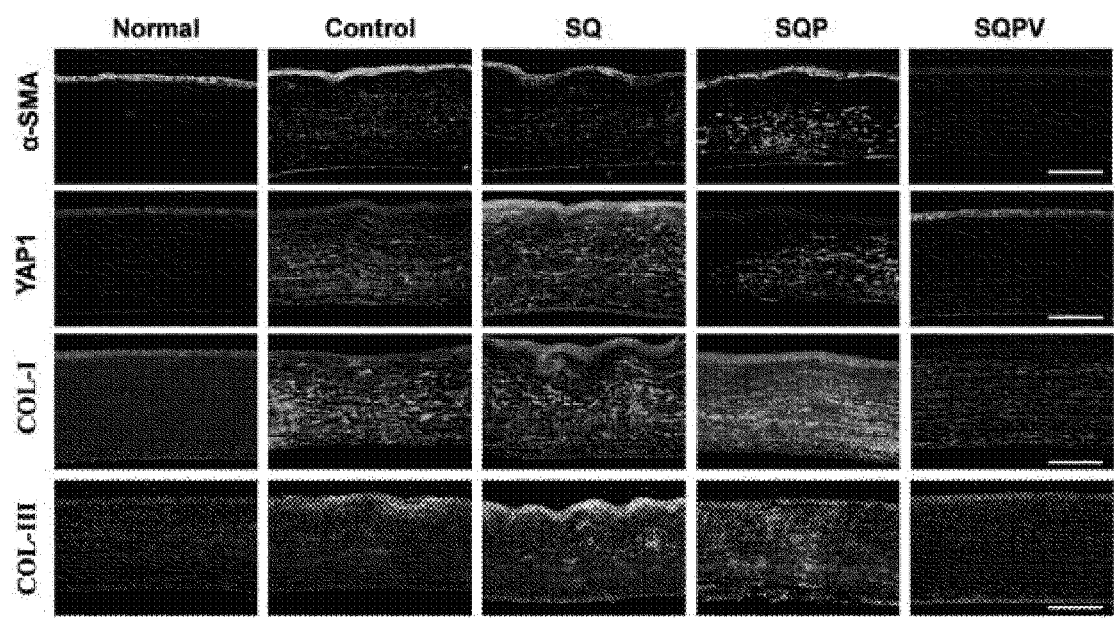
FIG. 14A is the immunofluorescence staining image of α-SMA, YAP1, COL-I and COL-III in cornea on the 28th day after treatment.
Figure 14B:
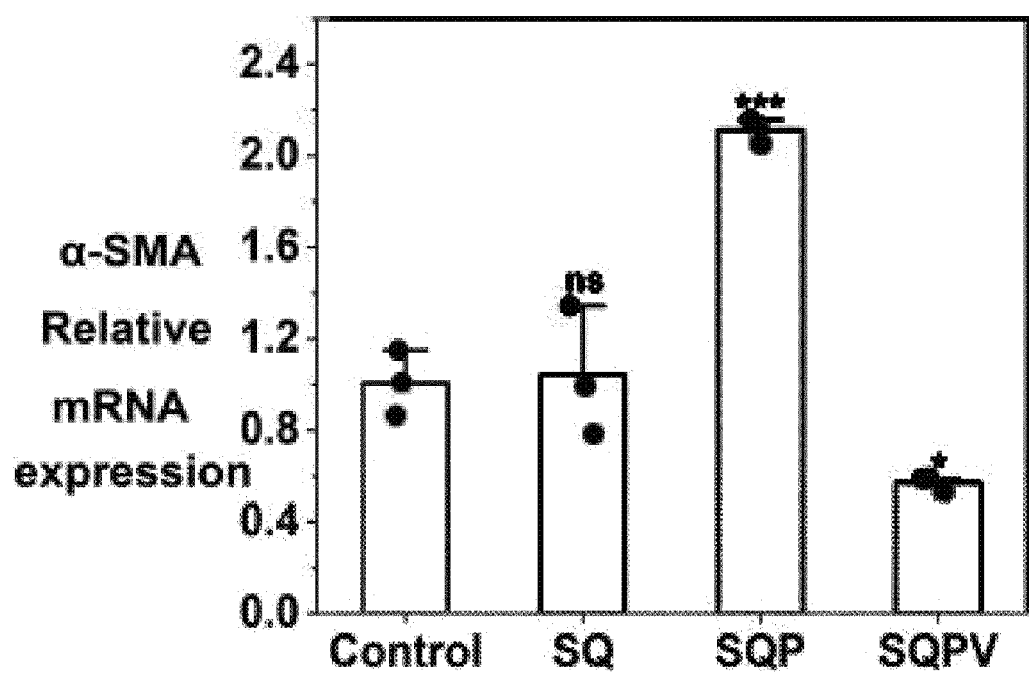
FIG. 14B is the result of RT-PCR analysis of α-SMA.
Figure 14C:
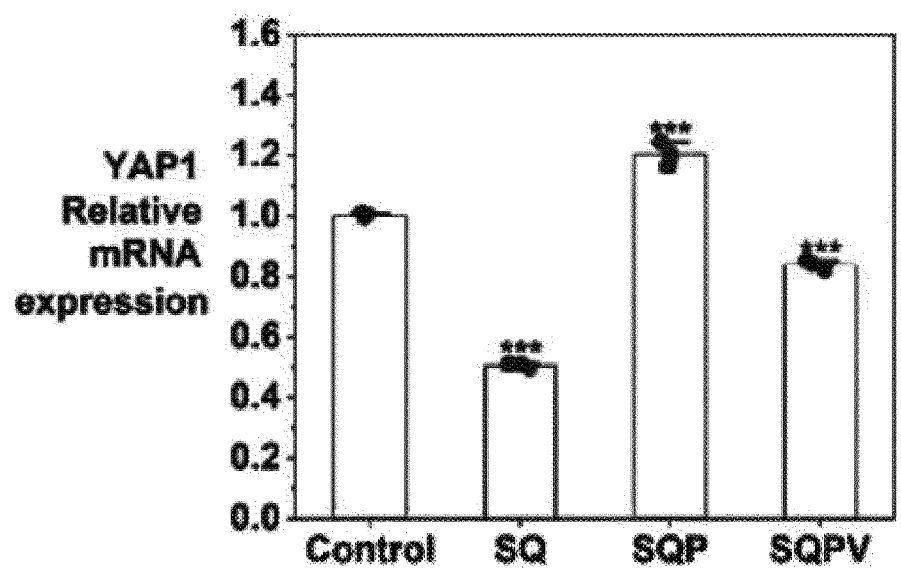
FIG. 14C is the result of RT-PCR analysis of YAP1.
Figure 14D:
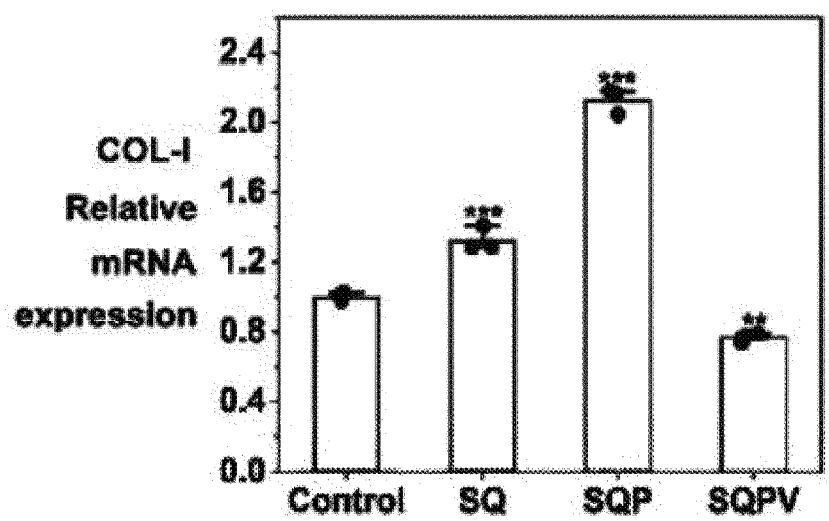
FIG. 14D is the result of RT-PCR analysis of COL-I.
Figure 14E:
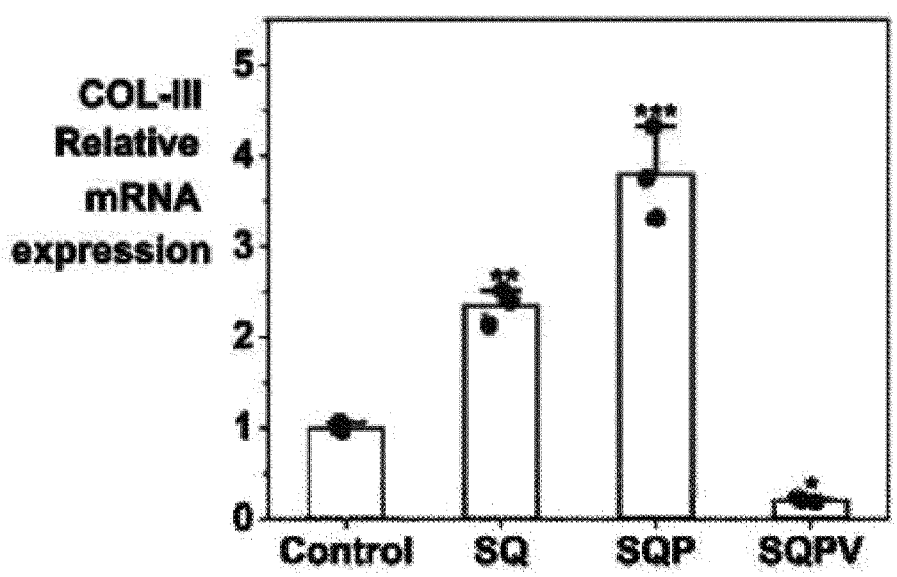
FIG. 14E is the result of RT-PCR analysis of COL-III.

The results of immunofluorescence staining and RT-PCR are shown in FIG. 14A-FIG. 14E, where FIG. 14A is the immunofluorescence staining image of α-SMA, YAP1, COL-I and COL-III in cornea on the 28th day after treatment (scale of 60 μm); FIG. 14B shows the results of RT-PCR analysis of α-SMA (n=3); FIG. 14C shows the results of RT-PCR analysis of YAP1 (n=3); FIG. 14D shows the results of RT-PCR analysis of COL-I (n=3); FIG. 14E shows the results of RT-PCR analysis of COL-III (n=3). According to FIG. 14A-FIG. 14E, the expression levels of α-SMA, YAP, COL-I and COL-III in the matrix treated with SQPV hydrogel are significantly reduced as compared with the other three groups, suggesting that SQPV hydrogel may reduce collagen deposition and tissue fibrosis, thus reducing scar formation.

The above results show that the present disclosure provides a preparation method of double-network versatile hydrogel with antibacterial and drug sequential release capabilities, and this double-network preparation method significantly improves the physical and chemical properties of hydrogel, making it an ideal substitute material for corneal transplantation. The double-network versatile hydrogel prepared by the present disclosure shows transparency and mechanical strength similar to that of natural cornea, with extremely strong adhesive strength at the same time, and may realize the functions of antibiosis, anti-inflammation, proliferation and reconstruction at different stages of corneal infection repair, thereby realizing controllable time and space sequential drug administration. The double-network versatile hydrogel provided by the present disclosure has great application potential in corneal repair and regeneration of severe bacterial keratitis.

The above-mentioned embodiments only describe the preferred mode of the present disclosure, and do not limit the scope of the present disclosure. Under the premise of not departing from the design spirit of the present disclosure, various modifications and improvements made by ordinary technicians in the field to the technical scheme of the present disclosure shall fall within the protection scope determined by the claims of the present disclosure.

What is claimed is:

1. A preparation method of a double-network versatile hydrogel with antibacterial and drug sequential release capabilities, comprising the following steps:
   (1) mixing 4-(4-hydroxymethyl-2-methoxy-5-nitrophenoxy) butyric acid, tert-butoxycarbonyl-polyethylene glycol-amino and 1H-benzotriazol-1-yloxytripyrrolidinophosphonium hexafluorophosphate in a solvent, and adding trifluoroacetic acid for reaction, and then concentrating and precipitating in a pre-cooled diethyl ether to obtain a precipitate;
   (2) re-dissolving the precipitate obtained in step (1), mixing with D/L-lactide, glycoluril and stannous isooctoate, concentrating after a reaction, and precipitating in a pre-cooled diethyl ether to obtain a precipitate;
   (3) co-blending the precipitate obtained in step (2) with a drug in a solvent and stirring to obtain drug-loaded micelles; and
   (4) mixing methacrylate silk fibroin, glycidyl methacrylate functionalized quaternized chitosan, polydeoxyribonucleotide, and lithium phenyl(2,4,6-trimethylbenzoyl) phosphinate with the drug-loaded micelles, followed by cross-linking under irradiation of ultraviolet to construct the double-network versatile hydrogel with antibacterial and drug sequential release capabilities.

2. The preparation method of the double-network versatile hydrogel with antibacterial and drug sequential release capabilities according to claim 1, wherein the mass ratio of the methacrylate silk fibroin to the glycidyl methacrylate functionalized quaternized chitosan is 5:1; the polydeoxyribonucleotide is present in an amount that is 0.01% of a total mass of the methacrylate silk fibroin and glycidyl methacrylate functionalized quaternized chitosan; the lithium phenyl(2,4,6-trimethylbenzoyl) phosphinate is present in an amount that is 0.2% of the total mass of the methacrylate silk fibroin and glycidyl methacrylate functionalized quaternized chitosan; and the drug-loaded micelles are present in an amount that does not exceed 1% of the total mass of the methacrylate silk fibroin and glycidyl methacrylate functionalized quaternized chitosan.

3. The preparation method of the double-network versatile hydrogel with antibacterial and drug sequential release capabilities according to claim 1, wherein a wavelength of the ultraviolet is 405 nm and a power is 3 W.

4. The preparation method of the double-network versatile hydrogel with antibacterial and drug sequential release capabilities according to claim 1, wherein the mass ratio of: 4-(4-hydroxymethyl-2-methoxy-5-nitrophenoxy) butyric acid to tert-butoxycarbonyl-polyethylene glycol-amino to 1H-benzotriazol-1-yloxytripyrrolidinophosphonium hexafluorophosphate to trifluoroacetic acid to D/L-lactide to glycoluril to stannous isooctoate is 0.25:5:1.5:0.15:0.2:0.05:0.005.

5. The preparation method of the double-network versatile hydrogel with antibacterial and drug sequential release capabilities according to claim 1, wherein the mass ratio of the precipitate obtained in step (2) to the drug is 5:1.

6. The preparation method of the double-network versatile hydrogel with antibacterial and drug sequential release capabilities according to claim 1, wherein the reaction duration in step (1) is 1 h; and the reaction temperature in step (2) is 130° C. and the reaction duration is 12 h.

7. A double-network versatile hydrogel with antibacterial and drug sequential release capabilities prepared by the method according to claim 1.

* * * * *